US00RE46379E

(19) United States
(12) Reissued Patent
Chen-Kiang et al.

(10) Patent Number: US RE46,379 E
(45) Date of Reissued Patent: Apr. 25, 2017

(54) FUNCTIONAL IMMUNOHISTOCHEMICAL CELL CYCLE ANALYSIS AS A PROGNOSTIC INDICATOR FOR CANCER

(71) Applicant: Cornell Research Foundation, Inc., Ithaca, NY (US)

(72) Inventors: Selina Chen-Kiang, New York, NY (US); Scott A. Ely, Pelham, NY (US); Maurizio DiLiberto, Rivervale, NJ (US)

(73) Assignee: Cornell Research Foundation, Inc., Ithaca, NY (US)

(21) Appl. No.: 14/964,240

(22) Filed: Dec. 9, 2015

Related U.S. Patent Documents

Reissue of:
(64) Patent No.: 8,603,763
Issued: Dec. 10, 2013
Appl. No.: 11/547,788
PCT Filed: Apr. 8, 2005
PCT No.: PCT/US2005/011929
§ 371 (c)(1),
(2) Date: May 7, 2007
PCT Pub. No.: WO2005/100999
PCT Pub. Date: Oct. 27, 2005

U.S. Applications:
(60) Provisional application No. 60/560,687, filed on Apr. 8, 2004.

(51) Int. Cl.
*G01N 33/574* (2006.01)
*G01N 33/48* (2006.01)

(52) U.S. Cl.
CPC ..... *G01N 33/57484* (2013.01)

(58) Field of Classification Search
CPC ..... G01N 33/574
USPC ..... 435/7.2, 40.52
See application file for complete search history.

(56) References Cited

U.S. PATENT DOCUMENTS

2010/0151447 A1 6/2010 Ely

FOREIGN PATENT DOCUMENTS

WO 2005/027907 A1 3/2005
WO WO2005/027907 * 3/2005

OTHER PUBLICATIONS

Schmitz et al., "Phosphorylation of the Retinoblastoma Protein in Childhood Acute Lymphoblastic Leukemia," Hematology 6:29-39 (2001).
Winfield et al., "Bone Marrow Histology 3: Value of Bone Marrow Core Biopsy in Acute Leukaemia, Myelodysplastic Syndromes, and Chronic Myeloid Leukaemia," J. Clin. Pathol. 45:855-59 (1992).
O'Connell et al., "CD138 (Syndecan-1), a Plasma Cell Marker. Immunohistochemical Profile in Hematopoietic and Nonhematopoietic Neoplasma," Am. J. Clin. Pathol. 121:254-63 (2004).
Leibundgut et al., "In Childhood Acute Lymphoblastic Leukemia the Hypophosphorylated Retinoblastoma Protein, P110RB, is Diminished, as Compared with Normal CD34 Peripheral Blood Prognitor Cells," Pediatric Research 45(5) (Part 1 of 2):692-96 (1999).
Hirt et al., "Site Specific Phosphorylation of Retinoblastoma Protein Due to Different Cyclin Dependent Kinase Activities in Childhood Acute Lymphoblastic Leukemia (ALL)," Blood 98(11 Part 2): 168 (abstract only), Nov. 2001.
Pui et al., "Clinical and Biologic Relevance of Immunologic Marker Studies in Childhood Acute Lymphoblastic Leukemia," 82:343-62 (1993).
Sivamurthy et al., "Attenuated Retinoblastoma Gene Product and Associate E2F/Retinoblastoma Imbalance in Anastomotic Intimal Hyperplasia," J. Vascular Surgery 35:1233-41 (2002).
Ito et al., "Cell Proliferation in Childhood Acute Leukemia," Cancer 69:2176-2182 (1992).
Soslow et al., "MIC2, TdT, bcl-2, and CD34 Expression in Paraffin-Embedded High-Grade Lymphoma/Acute Lympholastic Leukemia Distinguishes Between Distinct Clinicopathologic Entities," Human Pathol., 28(10):1158-64 (1997).
Urashima et al., "Interleukin-6 Promotes Multiple Myeloma Cell Growth Via Phosphorylation of Retinoblastoma Protein," Blood 88(6):2219-27 (1996).
Chilosi et al., "CD138/Syndecan-1: A Useful Immunohistochemical Marker of Normal and Neoplastic Plasma Cells on Routine Trephine Bone Marrow Biopsies," Modern Pathol. 12(12):1101-06 (1999).
Gondo et al., "HLA Class II Antigen Associated Invariant Chain Gene Expression in Malignant Lymphoma," British J. Haematology 67:413-17 (1987).
Kaiser, J., "First Pass at Cancer Genome Reveals Complex Landscape," Science 313:1370 (2006).
Montesano et al., "Genetic Alterations in Esophageal Cancer and Their Relevance to Etiology and Pathogenesis: A Review," Int. J. Cancer 69(3):225-35 (1996).
Lees et al., "The Retinoblastoma Protein Is Phosphorylated on Multiple Sites by Human cdc2," Embo J. 10(13): 4279-90 (1991).

(Continued)

*Primary Examiner* — Shri Ponnaluri
(74) *Attorney, Agent, or Firm* — LeClairRyan, a Professional Corporation

(57) ABSTRACT

The present invention relates to a method of determining the presence of a retinoblastoma protein (Rb)-mediated cancerous or pre-cancerous condition in a sample of fixed cells that involves exposing the sample to an antibody that recognizes phosphorylation of serine on the retinoblastoma protein (pS-Rb), and identifying cells in the sample that are recognized by the antibody to pS-Rb, where the recognition of pS-Rb in the sample determines the presence of an Rb-mediated cancerous or pre-cancerous condition. The method also involves identifying the presence of specific cell cycle markers and positive and negative cell cycle regulators to assess the stage of disease progression in a cancer patient having an (Rb)-mediated cancer. The present invention also relates to methods of assessing the efficacy of cancer therapy for an Rb-mediated cancer, determining the mechanism of cell cycle progression in an Rb-mediated cancer, and identifying cells predisposed to developing an Rb-mediated cancerous condition.

58 Claims, 6 Drawing Sheets

(56) References Cited

OTHER PUBLICATIONS

Zarkowska et al., Monoclonal Antibodies Specific for Underphosphorylated Retinoblastoma Protein Identify a Cell Cycle Regulated Phosphorylation Site Targeted by CDKs, Oncogene 14:249-54 (1997).
Stedman'S Medical Dictionary, 25th Ed., Hensyl et al., Eds., Baltimore, MD: Williams & Wilkins, pp. 1029-1030 (1990).
Kibel et al., "Loss of Heterozygosity at 12P12-13 in Primary and Metastatic Prostate Adenocarcinoma," J. Urology 164(1):192-6 (2000).
Dong et al., "Deletion at 13q21 Is Associated with Aggresive Prostate Cancers," Cancer Research 60:3880-83 (2000).
Zhau et al., "Biomarkers Associated with Prostate Cancer Progression," J. Cell Biochem. Suppl19:208-16 (1994).
Ren et al., "Reduced Lysyl Oxidase Messenger RNA Levels in Experimental and Human Prostate Cancer," Cancer Res. 58(6):1285-90 (1998).
Gingrich et al., "Metastic Prostate Cancer in a Transgenic Mouse," Cancer Res. 56(18):4096-102 (1996).
Russo et al., "Expression of the Mage Gene Family in Primary and Metastatic Human Breast Cancer: Implications for Tumor Antigen-Specific Immunotherapy," Int. J. Cancer 64:216-21 (1995).
Ely et al., "Plasma Cell Proliferation Index As a Clinical Prognosticator for Relapsed Multiple Myeloma," IXth Internat'l Workshop on Myeloma, Salamanca, Spain, May 26, 2003, Hematol. J 4S:169, Abstract #184 (2003).
International Search Report for PCT/US05/11929 dated Nov. 22, 2006.
Zarkowska et al, 1997,14: 249-254.*
Stedman's medical dictionary, 25th ed, 1990, p. 1029-1030.*
Kibel, AS et al, 2000, J urol, 164(1): 192-6.*
Dong et al, 2000, Cancer Research, 60: 3880-3883.*
Zhau, HE, 1994, J Cell Biochem, Suppl 19: 208-216.*
Ren, C et al, 1998, Cancer Res, 58(6): 1285-90.*
Gingrich, JR et al, 1996, Cancer res, 56(18): 4096-4102.*
Russo, V et al, 1995, Int J Cancer, 64: 216-221.*
Gondo et al, 1987, British J Haematology, 67: 413-417.*
Kaiser, 2006, Science, 313: 1370.*
Montesano, R et al, 1996, Intl J Cancer, 69(3): 225-235.*
Lee et al, 1991, EMBO J, 10(13): 4279-4290.*
Leibundgut et al, 1999, Pediatric Research, 45(5, part 1 of 2): 692-696.*
Hirt et al, 2001, Blood, 98 (11 Part 2): 168.*
Pui et al, 1993, Blood, 82: 343-362.*
Sivamurthy et al,2002, J Vascular Surgery, 2002, 35: 1233-41.*
Ito et al, 1992, Cancer, 69: 2176-2182.*
Soslow et al, 1997, Human Pathol, 28(10): 1158-1164.*
Urashima et al, 1996, Blood, 88 (6): 2219-2227.*
Chilosi et al, 1999, Modern Pathol, 12(12): 1101-1106.*
Schmitz et al (Hematology, 2001, vol. 6, pp. 29-39).*
Winfield and Polacraz (Journal of Clinical Pathology, 1992, vol. 45, pp. 855-859).*
O'Connell et al (American Journal of Clinical Pathology, 2004, vol. 121, pp. 254-263).*
Kanavaros et al., "Immunohistochemical Expression of the p53, p21/Waf-1, Rb, p16 and Ki67 Proteins in multiple Myeloma," Anticancer Res. 20:4619-4626 (2000).
Alexandrakis et al., "The Relation Between Bone Marrow Angiogenesis and the Proliferation Index Ki-67 in Multiple Myeloma," J. Clin. Pathol. 57:856-860 (2004).
Hans et al., "Confirmation of the Molecular Classification of Diffuse Large B-Cell Lymphoma by Immunohistochemistry Using a Tissue Microarray," Blood 103:275-282 (2004).
Van Der Loos et al., "Practical Suggestions for Successful Immunoenzyme Double-Staining Experiments," Histochem. J. 25:1-13 (1993).
Office Action in U.S. Appl. No. 12/641,240 (dated Aug. 14, 2012).
Barrie et al., "High-Throughput Screening for the Identification of Small-Molecule Inhibitors of Retinoblastoma Protein Phosphorylation in Cells," Anal. Biochem. 320:66-74 (2003).
Dalton et al., "Multiple Myeloma," Hematology, pp. 157-177 (2001).
Klasa et al., "Rational Approaches to Design of Therapeutics Targeting Molecular Markers," Hematology, pp. 443-462 (2001).
Park et al., "Arsenic Trioxide-Mediated Growth Inhibition in MC/CAR Myeloma Cells via Cell Cycle Arrest in Association with Induction of Cyclin-Dependent Kinase Inhibitor, p21, and Apoptosis," Cancer Res. 60:3065-3071 (2000).
Park et al., "Monensin-Mediated Growth Inhibition in NCI-H929 Myeloma Cells via Cell Cycle Arrest and Apoptosis," Int. J. Oncol. 23(1):197-204 (2003).
Sherr, C.J., "Cancer Cell Cycles," Science 274:1672-1677 (1996).
Urashima et al., "Interleukin-6 Overcomes p21WAF1 Upregulation and G1 Growth Arrest Induced by Dexamethasone and Interferon-γ in Multiple Myeloma Cells," Blood 90(1):279-289 (1997).

* cited by examiner

FUNCTIONAL IMMUNOHISTOCHEMICAL CELL CYCLE ANALYSIS AS A PROGNOSTIC INDICATOR FOR CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the benefit of U.S. Provisional Patent Application Ser. No. 60/560,687, filed Apr. 8, 2004, which is hereby incorporated by reference in its entirety.

FIELD OF THE INVENTION

The present invention relates to immunohistochemical methods for functional assessment of cell cycle progression of cells in situ as a prognostic indicator of disease progression in hematopoietic cancers and as a measure of cancer therapy efficacy in cancer patients.

BACKGROUND OF THE INVENTION

Cancers are, in general, classified by the cell type and site of origin, such as lymph node, lung, bone marrow, etc. In addition, they are sub-classified based on histologic characteristics and the proteins expressed by the cancer cells, as determined by immunophenotyping. These sub-types define biologically distinct diseases, each of which has its own distinct clinical behavior and, hence, its own specific therapy. For example, the most common testicular cancer, seminoma, is treated and in most cases cured with radiation, whereas the non-seminomatous testicular cancers do not respond to radiation therapy. Similarly, among blood cancers, lymphoblastic leukemia, the most common malignancy in childhood, can be cured by multi-agent chemotherapy, but multiple myeloma, one of the most common lymphoid cancers in adults, is invariably fatal. Cancer sub-typing, along with the degree of cancer spreading (stage) and the underlying health of the patient, is therefore a critical consideration for choice of therapy. However, although cancer sub-typing contributes to prognostic and therapeutic decisions and statistically significant outcomes can be obtained from studies of large cohorts of patients, considerable variability in disease outcome exists among individuals of stage-matched patients in most cancer subclasses. It is particularly difficult to predict the outcome of pre-malignant lesions.

Cancer cells by definition are monoclonal, arising from inappropriate expansion of one single cell that has lost controls in both cell cycle (proliferation) and apoptosis (cell death). In normal cells, it is well established that cell cycle progression is controlled by the balance between positive and negative cell cycle regulators, and not by a single cell cycle regulator. However, the mechanism that underlies the loss of cell cycle control in each cancer type is not understood. Thus far, cell cycle dysregulation in cancers is often assayed at the DNA level by the analysis of gene deletion and mutation, at the RNA level by RT-PCR analysis or microarray, or at protein expression level by immunohistochemistry or Western blotting when the appropriate antibodies are available. These types of analyses are informative with regard to the altered expression of a specific gene, but do not reveal the net balance between positive and negative cell cycle regulators required to control cell cycle progression.

The cell cycle is divided into 4 phases (G1, S, G2, and M), as shown in FIG. 2A. Cell cycle progression is a multi-step process, and each step is controlled by the distinct balance, in molar ratios, between positive regulators (cyclin dependent kinases (CDK or cdk) and cyclins) and negative regulators (cyclin dependent kinase inhibitors (CDKI)). The mammalian cell cycle is controlled by cytokines and growth factors predominantly at the G1 phase of the cell cycle, the first growth phase following cell division or cell cycle entry. G1 can be subdivided into two phases, the early and late G1 phases, by the mid-G1 restriction point, characterized by phosphorylation of the retinoblastoma (Rb) protein by CDK4 or CDK6 on specific serine sites (called pS-Rb). Rb is the prototype tumor suppressor protein and is a major target for mutations in cancer (Sherr C J, "Cancer Cell Cycles," Science 274:1672-1677 (1996)). Rb is inactivated in most tumors, either by mutation of the Rb gene or by hyperphosphorylation of the protein as a result of other events in the Rb pathway (Sherr C J, "Cancer Cell Cycles," Science 274:1672-1677 (1996)). The controls of early and late G1 are distinct. To prepare for cell division, a cell must synthesize new DNA in the "S" phase of the cell cycle, which can be marked by the uptake of nucleotide analogues such as BrdU (5'-deoxybromouridine). Thus, analysis of G1 progression before S phase entry at the single cell level by immunohistochemistry represents an effective means of assessing G1 cell cycle progression, and, therefore, the expansion of cancer cells and disease progression.

It was previously established that one specific INK4 family of the CDK inhibitors, p18INK4c, is required for the generation of normal, functional plasma cells (Morse et al., "Induction of Cell Cycle Arrest and B Cell Terminal Differentiation by CDK Inhibitor $p18^{INK4c}$ and IL-6," Immunity 6:47-56 (1997); Tourigny et al., "CDK Inhibitor $p18^{INK4c}$ is Required for the Generation of Functional Plasma Cells," Immunity 17:179-189 (2002)), that p18 expression is lost in some but not all myeloma cells, and that p18 deficiency leads to the development of pituitary adenomas in older mice (Franklin et al., "CDK Inhibitors $p18^{INK4c}$ and $p27^{Kip1}$ Mediate Two Separate Pathways to Collaboratively Suppress Pituitary Tumorigenesis," Genes Dev 12:2899-2911 (1998)). At least one other INK4 family protein, p16, has also been implicated in myeloma pathogenesis because it is silenced by promoter hyper-methylation. However, there is no direct evidence that loss of a single INK inhibitor is sufficient to cause cancer. Overexpression of positive cell cycle regulators such as cyclin D1 or D3 has also been implicated in myeloma pathogenesis. However, the expression of cyclin D1 or D3 in myeloma cells bears no relationship to the cell cycle status. Together, these findings reinforce the critical importance of determining the balance, and not the expression of a single cell cycle regulator, as an indicator of cell cycle progression in cancers such as myeloma.

Control of cell cycle re-entry and the progression from G1 to S phase regulates physiologic responses, and loss of this control can be critical for oncogenesis (Sherr et al., "Living With or Without Cyclins and Cyclin-Dependent Kinases," Genes Dev 18:2699-711 (2004)).

D cyclins are essential for development beyond the early embryonic stage and for the hematopoietic lineage, including B-lymphocytes (Kozar et al., "Mouse Development and Cell Proliferation in the Absence of D-Cyclins," Cell 118: 477-91 (2004)). Cyclin D2, in particular, is expressed in B cells, the precursors of antibody secreting plasma cells (PCs), and is needed for cell cycle activation in response to physiologic signals (Tanguay et al., "Regulation of the Catalytic Subunit (p34PSK-J3/cdk4) for the Major D-Type Cyclin in Mature B Lymphocytes," J Immunol 156:539-48 (1996); Solvason et al., "Cyclin D2 is Essential for BCR-Mediated Proliferation and CD5 B Cell Development," Int Immunol 12:631-8 (2000)). Following activation by antigen, inhibition of Cdk6 by the early G1 CdkI, p18INK4c (Guan et al., "Growth Suppression by p18, a p16INK4/MTS1- and p14INK4B/MTS2-Related CDK6 Inhibitor, Correlates with Wild-Type pRb Function," Genes Dev 8:2939-52 (1994); Hirai et al., "Novel INK4 Proteins, p19 and p18, are Specific Inhibitors of the Cyclin D-Dependent Kinases CDK4 and CDK6," Mal Cell Biol 15:2672-81 (1995)), is specifically required for G1 cell cycle arrest and terminal differentiation to PCs (Morse et al., "Induction of Cell Cycle Arrest and B Cell Terminal Differentiation by CDK Inhibitor p18(INK4c) and IL-6," Immunity 6:47-56 (1997); Tourigny et al., "CDK Inhibitor p18(INK4c) is Required for the Generation of Functional Plasma Cells," Immunity 17:179-89 (2002)). Thus, B cell development and function requires specific D cyclins, Cdk4/6, and CdkIs, implying that perturbation of this balance is likely to underlie oncogenesis in the B lineage.

Plasma cells (PCs) are terminally differentiated B cells that secrete immunoglobulin (Ig). Multiple myeloma (MM) is a cancer of plasmacytoid cells that are arrested from terminal differentiation. MM cells reside in the bone marrow (BM) and secrete a monoclonal Ig detected in the peripheral blood. Morbidity and mortality associated with MM are due to bone lysis and fractures, renal failure, and infections. MM is uniformly fatal with an average survival of 3 years, a statistic that has not changed in the past 40 years (Survey Epidemiology and End Results Data. National Cancer Institute website.) Moreover, MM is becoming more prevalent. It is now the second most common blood cancer and the third fastest growing of all cancers in patients 65 and under. It is twice as common in African Americans as in Caucasians.

MM is diagnosed by a clinical scoring system based on blood tests, radiological studies and finding a minimum number of PCs in a liquid marrow aspirate (International Myeloma Working Group, "Criteria for the Classification of Monoclonal Gammopathies, Multiple Myeloma and Related Disorders: A Report of the International Myeloma Working Group," Br J Haematol 121(5):749-57 (2003)). Although a BM tissue core biopsy (BMBX) is routinely taken along with the aspirate, BMBX findings are not part of any diagnostic or staging system (Ely S A, "Diagnosis and Management of Multiple Myeloma," Br J Haematol 118(4): 1194-5 (2002)). However, studies show that biopsy criteria can provide powerful prognostic information in MM (Sailer et al., "Prognostic Relevance of a Histologic Classification System Applied in Bone Marrow Biopsies from Patients with Multiple Myeloma: a Histopathological Evaluation of Biopsies from 153 Untreated Patients," Eur J Haematol 54(3):137-46 (1995)). Chromosomal changes in large cohorts correlate statistically with prognosis, but the associations are inconsistent and not explained by biologic data. Patients are staged by peripheral blood biomarkers. Treatment is based only on staging and overall health (Richardson et al., "A Phase 2 Study of Bortezomib in Relapsed, Refractory Myeloma," N Engl J Med 348(26):2609-17 (2003); International Myeloma Working Group, "Criteria for the Classification of Monoclonal Gammopathies, Multiple Myeloma and Related Disorders: A Report of the International Myeloma Working Group," Br J Haematol 121(5): 749-57 (2003); Weber et al., "Confirmation of Prognostic Value of Model Using B2-Microglobulin (B2M) and Albumin for Multiple Myeloma (MM) Proposed by the International Myeloma Working Group (IMWG) with Similar Results Using B2M Alone," Abstract #3491 Blood 102(11) (2003); Greipp et al., "A New International Staging System (ISS) for Multiple Myeloma (MM) from the International Myeloma Working Group," Abstract #664 Blood 102 (11) (2003)).

The importance of dividing patients based on biologic features is underscored by the success of the plasma cell labeling index (PCLI) (Greipp et al., "Clinical, Morphological, and Cell Kinetic Differences Among Multiple Myeloma, Monoclonal Gammopathy of Undetermined Significance, and Smoldering Multiple Myeloma," Blood 62(1):166-71 (1983)). The PCLI is an ex vivo assay using BrdU incorporation in live PCs from BM aspirates to compute the percentage in S phase of the cell cycle (CC). Prior to the present invention, it was the most powerful prognosticator in MM. However, the method is costly, labor intensive, and requires specialized equipment not available in most hospitals. Also, because it requires live PCs, it can only be performed immediately after an aspirate is drawn. Thus, 20 years after being published, the PCLI only is used in a few research centers. However, PCLI data shows that CC status may be the key biologic feature that differentiates patients.

Although several promising drugs are available, they are utilized based on clinical discretion alone. Aside from the expanded arsenal of drugs and additional blood tests that have improved staging criteria, this system has changed little since the mid-1970s (Greipp et al., "A New International Staging System (ISS) for Multiple Myeloma (MM) from the International Myeloma Working Group," Abstract #664 Blood 102 (11) (2003)). The current standard of care for some cancers, including, but not limited to non-solid cancers such as multiple myeloma, is to provide no treatment when the patient is in plateau phase, and wait for a relapse to treat the patient.

In the past few years, significant advances have been made in caring for patients with multiple myeloma (MM), the second most common hematopoietic cancer. For the first time since the early 1960s, promising new drugs are available (Richardson et al., "A Phase 2 Study of Bortezomib in Relapsed, Refractory Myeloma," N Engl J Med 348(26): 2609-17 (2003)). However, for optimistic expectations to come to fruition, advances in drug development must be paralleled by advances in how patients are evaluated. The current practice of lumping patients together based only on the extent of disease (stage) rather than separating them into subgroups based on biologic differences belies the heterogeneity of diseases under the MM rubric. Systems for dividing patients based on biopsy findings have lead to increased longevity for patients with Hodgkin lymphoma, testicular, and other common cancers (see "Survey Epidemiology and End Results Data" available on the National Cancer Institute website). To make a similar impact on the survival of patients with MM, a system for predicting which patients will benefit from what therapy must be found. Understanding such cell cycle deregulation will allow for more specific diagnosis of disease state, and afford an opportunity to intervene with better therapeutic approaches designed to treat cancer at different stages of the disease condition.

The present invention is directed to overcoming these and other deficiencies in the art.

SUMMARY OF THE INVENTION

A first aspect of the present invention relates to a method of determining the presence of a retinoblastoma protein (Rb)-mediated cancerous or pre-cancerous condition. This method involves providing a patient sample having fixed cells, exposing the patient sample to an antibody that recognizes phosphorylation of serine on the retinoblastoma protein (pS-Rb), and identifying cells of the patient sample that are recognized by the antibody to the pS-Rb protein. The recognition of pS-Rb in the cells of the patient sample determines the presence of an Rb-mediated cancerous or pre-cancerous condition.

A second aspect of the present invention relates to a method of determining the presence of a retinoblastoma protein (Rb)-mediated cancerous or pre-cancerous condition. This method involves providing a first and a second patient sample each having fixed cells, the second patient sample having been obtained from the same patient after a time delay. The first and second patient samples are exposed to an antibody that recognizes phosphorylation of serine on the retinoblastoma protein (pS-Rb), and cells of the patient samples that are recognized by the antibody to the pS-Rb protein are identified. The method also involves determining whether the second patient sample, relative to the first patient sample, contains a change in the percentage of cells that are recognized by the antibody to the pS-Rb protein. An increase indicates advancement of the Rb-mediated cancerous or pre-cancerous condition, and a decrease indicates an indolent or clinical plateau phase of the Rb-mediated cancerous or pre-cancerous condition.

A third aspect of the present invention relates to yet another method of determining the presence of a retinoblastoma protein (Rb)-mediated cancerous or pre-cancerous condition. This method involves providing a patient sample having fixed cells, exposing the patient sample to an antibody that recognizes phosphorylation of serine on the retinoblastoma protein (pS-Rb), and identifying cells in the patient sample that are recognized by the antibody to the pS-Rb protein. This method involves also exposing the patient sample to an antibody that recognizes a nuclear marker for a cell cycling protein, and identifying cells in the patient sample that are recognized by an antibody for the nuclear cell cycling protein marker. The presence of pSRb and cell cycling protein marker positive cells in the patient sample determines the status of cell cycle regulation in Rb-mediated cancerous or pre-cancerous conditions.

A fourth aspect of the present invention relates to a method of assessing the stage of disease progression in a cancer patient having a retinoblastoma protein (Rb)-mediated cancer. This method involves performing the method according to the first aspect of the invention on a patient sample to identify cells that are recognized by the antibody to pS-Rb protein, exposing the patient sample to one or more antibodies that recognize positive cell cycle regulators, exposing the patient sample to one or more antibodies that recognize a cell surface marker for neoplastic cells, and determining whether cells in the patient sample that are recognized by the anti-pSRb antibody are recognized by the one or more antibodies for the positive cell cycle regulators, and/or the one or more antibodies for cell surface markers for neoplastic cells, thereby assessing the progression of disease in the cancer patient.

A fifth aspect of the present invention relates to a method of assessing the efficacy of cancer therapy for a retinoblastoma protein (Rb)-mediated cancer. This method can be carried out by performing the method according to the second aspect of the invention to identify cells in the first and second patient samples that are recognized by the antibody to pS-Rb protein. Because the first and second samples are obtained from the patient before and after, respectively, administration of cancer therapy to the patient, a decrease in the percentage of identified cells in the second patient sample, relative to the first patient sample, indicates the efficacy of the cancer therapy.

A sixth aspect of the present invention relates to a method of determining the mechanism of cell cycle progression for cells in a patient sample. This method is carried out by performing the method according to the first aspect of the invention to identify cells in the sample that are recognized by the antibody to pS-Rb protein, identifying the presence of positive or negative cell cycle regulators in the patient sample; and assessing whether the identified cells in the patient sample possess one or more of the positive or negative cell cycle regulators, thereby determining the mechanism of cell cycle progression in the patient sample.

A seventh aspect of the present invention relates to a method of identifying a cell predisposed to developing a retinoblastoma protein (Rb)-mediated cancerous condition. This method is carried out by performing the method according to the third aspect of the present invention on a patient sample, wherein at least one cell in the patient sample is positive for both pS-Rb and a cell cycling protein marker, and exposing the patient sample to one or more antibodies that recognize negative cell cycle regulators, wherein low or undetectable expression of the negative cell cycle regulators in a cell indicates predisposition of the cell to becoming cancerous.

The present invention provides oncology professionals with the tools for early diagnosis and personalized prognostication of precancerous or cancerous conditions, and the ability to monitor and predict treatment efficacy based on an individual patient's response to therapy at the cellular level. The present invention provides for an improvement over the current standard of cancer care. For example, periodic testing of the patient's pS-Rb status according to the present invention can provide evidence that the patient's cells have begun re-entry into the proliferative stage following a quiescent period. The presence of pS-Rb in greater than 10% of the cells signifies an eminent relapse and triggers a treatment decision. Further characterization of the patient's disease status can be obtained from immunostaining for other cell-cycle proteins (as described hereinafter).

BRIEF DESCRIPTION OF THE DRAWINGS

FIG. 2A shows that serine phosphorylation of Rb by cdk/cyclin complexes during G1 causes the release of Rb-bound E2F, resulting in S phase transition. G1 progression depends upon the molar ratio of positive to negative regulators. FIG. 2B shows patient bone marrow biopsies double immunostained for CD138 (red) and (cell cycle) proteins (brown) (serine 780 phosphorylated Rb (pS780), serine 807/811 phosphorylated Rb (pS807/811)). In a normal biopsy (PT1239) and in a newly diagnosed, untreated, early MM (247-1), the PCs are not cycling (i.e., do not express Ki-67). Rb may be expressed but is not phosphorylated. At the time of relapse (247-2), Rb is up-regulated, most of which is phosphorylated; Ki-67 also is increased. Calyculin A (CA; a phosphatase inhibitor) treatment showed a negligible increase in the intensity of phosphorylated signals and had no affect on non-phosphorylated signals. Calf intestinal phosphatase (CIP) eradicated phosphospecific signals but had no effect on non-phosphorylated epitopes. A primary retinal retinoblastoma with biallelic inactivation of the Rb gene showed the absence of Rb and of the plasma cell antigen, CD138, but strong expression of Ki-67. FIG. 2C is a graph showing a linear correlation between ex vivo BrdU incorporation and expression of Ki-67, pS780, and the minichromosome maintenance proteins (MCM2 and MCM7) which are involved in DNA synthesis. Error bars show standard error of triplicate analyses.

FIGS. 3A-B are graphs showing the frequency of MM cells expressing cyclin D1, (FIG. 3A), or D3 (brown) (FIG. 3B), and CD138 (red), determined in 251 mM patients by immunohistochemistry (IHC) and counting 450 CD138+ BM cells (150 cells in each of 3 separate areas) in each section. The analyses of cyclin D1 and D3 (brown) were performed on serial BM biopsies. (MGUS, monoclonal gammopathy of undetermined significance; MM, multiple myeloma; new, newly diagnosed and untreated; Tx, treated). FIG. 3C is a representative IHC analysis of pS807/811, Ki-67, and CD20 expression (all brown), determined on serial sections as in FIGS. 3A-B. FIG. 3D shows a frequency analysis of D1 and Ki-67 expression in CD138+ cells of all 251 patients, determined as in FIGS. 3A-B.

FIG. 5A shows the immunohistochemistry analysis for simultaneous expression of CD138 (red) with Rb phosphorylation (pS780), Rb, Cdk6, Ki-67, cyclin D1 or cyclin D3 in serial sections of bone marrow core biopsies (BMBxs). Analysis of initial BMs from stage 1, Table III (see below), showed either uniform D1 expression, accompanied by occasional pS780 but not Ki-67 (336) or complete absence (346, 137-1). However, at the time of disease progression (137-2, 14 months later), although most of the MM cells were still negative (4th column), there were discrete foci of MM cells with strong expression of Cdk6, Rb and pS780, still in the absence of D1, D3 and Ki-67 (5th column). FIG. 5B is an immunoblot analysis of G1 cell cycle regulatory proteins in purified CD138+ BMPC from a volunteer control (Tourigny et al., "CDK Inhibitor p18 (INK4c) is Required for the Generation of Functional Plasma Cells," Immunity 17(2):179-89 (2002), which is hereby incorporated by reference in its entirety), and patients 336 and 346 (shown in FIG. 5A). The ratios between pS780 and total Rb are shown at the bottom. FIG. 5C shows the relative RNA levels from the same cells, determined by real-time RT-PCR analysis. These results represent nine independent analyses of the cells from FIG. 5A, and three independent analyses of the cells of FIG. 5B and FIG. 5C.

FIG. 6A is an IHC analysis of simultaneous expression of CD138 (red) and Rb phosphorylation, Rb, cyclin D1 (D1), cyclin D3 (D3), p18INK4c (p18) or p27Kip1 (p27) (all brown) in BM core biopsy sections of a volunteer control (Tourigny et al., "CDK Inhibitor p18(INK4c) is Required for the Generation of Functional Plasma Cells," Immunity 17(2):179-89 (2002), which is hereby incorporated by reference in its entirety), an MGUS patient (376), an untreated stage 1 mM patient expressing Rb in a rare cell (inset) (329), a stage III untreated MM patient (327) and a stage IIIA treated and relapsed MM patient (243). The nuclei were counter-stained with hematoxylin (blue). FIG. 6B is an immunoblot analysis of G1 cell cycle regulatory proteins in purified CD138+ bone marrow plasmacytoid cells from the same patients shown in FIG. 6A. The actin level serves as a loading control. The ratios between pS780 and total Rb are shown at the bottom. FIG. 6C is an immunoblot analysis of Cdk6, Cdk4, and p27Kip1 present in the cyclin D2 immune complexes, or cyclin D2 and p27Kip1 present in the Cdk6 immune complexes, in CD138+ BM cells of the stage III patient BM243. Pre-incubation with the cyclin D2 or Cdk6 blocking peptide is as indicated. FIG. 6D are graphs showing the relative RNA levels from the same cells shown in FIG. 6B, determined by real-time RT-PCR. The data represent ten independent analyses of FIG. 6A and three independent analyses of FIGS. 6B-6D of the same specimens.

DETAILED DESCRIPTION OF THE INVENTION

Figure 1:
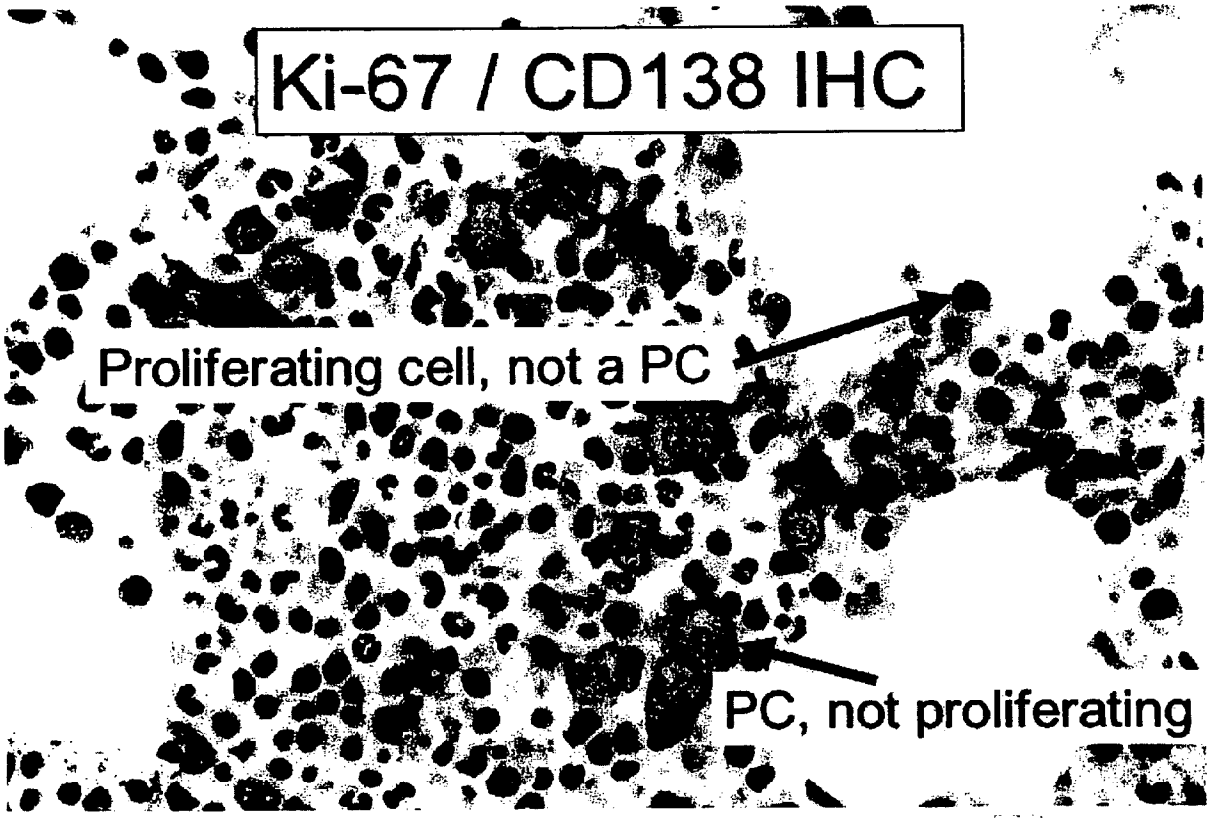
FIG. 1 shows the result of immunohistochemical (IHC) analysis performed on a bone marrow tissue core biopsy (BMBX) utilizing antibodies against cell cycling protein Ki-67 (brown nuclear signal expressed in all cycling cells), and neoplastic cell marker CD138 (red cell membrane signal expressed only in plasma cells (PCs)). Negative nuclei are counter-stained blue. This assay enables one to tell how many of the PCs (red membrane) are cycling (brown nucleus) or not (blue nucleus) (e.g., no PCs in this BMBX from a normal patient are cycling).

The present invention relates to methods of screening patient samples to determine (i) the presence of a retinoblastoma protein (Rb)-mediated cancerous or pre-cancerous condition, (ii) the stage of Rb protein-mediated cancer in a cancer patient, (iii) the efficacy of cancer therapies, (iv) the mechanism of cancer cell cycle progression in Rb protein-mediated cancers, and (v) predisposition of a patient to develop an Rb protein-mediated cancerous condition.

One aspect of the present invention relates to a method of determining (i.e. diagnosing) the presence of an Rb protein-mediated cancerous condition. This method of the invention involves exposing the patient sample to an antibody that recognizes phosphorylation of serine on the retinoblastoma protein (pS-Rb), and identifying cells in the patient sample that are recognized by the antibody to the pS-Rb protein. The recognition of pS-Rb in cells of the patient sample allows for determining the presence of an Rb-mediated cancerous or pre-cancerous condition.

The Rb-protein contains multiple serine residues. Phosphorylation of serine on the retinoblastoma protein (designated as pS-Rb) as used herein is meant herein to include the phosphorylation of any serine residue on the Rb protein, including, without limitation, a serine at amino acid position 608 (serine$^{608}$), position 780 (serine$^{780}$), position 795 (serine$^{795}$), and positions 807/811 (serine$^{807/811}$). Therefore, pS-Rb antibodies suitable for this aspect of the present invention include any antibody that recognizes the phosphorylation of a serine residue of the Rb protein, preferably those identified above. As described above, the presence of pS-Rb indicates that the cell has entered the mid-G1 phase of cell cycle progression, and is, therefore, on the path to cell division. Thus, in an immunohistochemical analysis of pS-Rb including samples from newly diagnosed, untreated patients, from patients in relapse, and from patients in stable/plateau phase of disease, the expectation would be for pS-Rb expressing cells to compose a high proportion of the total cell number in the relapsed patient sample (ratio=0.50-1.0); low or intermediate proportion in stable/plateau phase sample (ratio=0.10-0.50); and, usually, low proportion in newly diagnosed patients (ratio=0.01-0.09). However, a minority of patients present with an unusually aggressive disease in which the proportion of pS-Rb+ cells is expected to be high. Thus, the present invention is to able to predict which newly diagnosed patients will need treatment right away and which can be observed for some time. As used herein "plateau" or "plateau phase" means that the patient is not in remission, i.e., still has cancer, but from a clinical perspective, the disease is not progressing, i.e. the stage or extent of disease is stagnant. "Plateau phase" is used most often to describe myeloma, but can be used to describe other hematopoietic cancers. In chronic myelogenous leukemia (CML), it is usually referred to as the "stable phase."

Each of the methods of the present invention involve obtaining one or more patient samples and exposing the samples(s) to one or more antibodies that recognize (i.e., have specificity for) a marker of interest. Depending upon the antibody or combination of antibodies employed, it is possible to make the above-listed determinations based upon antibody reactivity with the patient sample(s). Where multiple antibodies are used concurrently (i.e., in a single assay), it is preferable for each antibody to have a different label to allow for discrimination thereof. Fluorescent labels are preferred, but other known labels can also be employed.

The patient samples that are reacted with the one or more antibodies are preferably fixed. One of the improvements of the present invention over the current methodologies is that the immunohistochemical analysis of all embodiments of the present invention may be carried out on a patient sample that is fixed. Obtaining a bone marrow or tumor biopsy sample from the patient, fixing and embedding it, taking serial sections, and treating the sections immunohistochemically according to the present invention requires only routine procedures. Because the present invention is designed to work on routinely processed specimens, no deviation from the standard protocol for pathology specimen handling and diagnosis is required for the analysis. The assays can be performed on any type of specimen, including, without limitation, a small endoscopic gastric biopsy, a large lung cancer resection specimen, a bone marrow core biopsy, etc. After the specimen is received, it is preserved in a fixative (e.g., 10% neutral buffered formalin). After fixation, the specimen is embedded (e.g., in paraffin wax) and histologic sections are cut by a microtome and stained for microscopic examination. Routinely stained (hematoxylin and eosin) sections are examined by a pathologist. A diagnosis is established either by routine microscopy alone or in combination with an immunophenotypic analysis, as is routinely employed to diagnose certain types of cancers. Then the pathologist can request that additional histologic slides be immunostained for cell cycle analysis according to the present invention. Alternatively, the clinician treating the patient or the patient can request that slides be sent for the analyses encompassed by the present invention. Because the assays are performed on routinely preserved tissue, a treating physician may request that the assays be performed retrospectively. For example, a biopsy taken at relapse may be analyzed alongside the archived original diagnostic biopsy; then a comparison could be made between the state of the cell cycle at the time of the original diagnosis and at relapse.

As used herein, the terms "cancer" and "pre-cancerous condition" refer to Rb protein-mediated cancers, particularly but not exclusively B cell cancers and/or T cell cancers. Exemplary Rb protein-mediated cancers include, without limitation, all acute myelogenous leukemias (AML); acute promyelocytic leukemia (APL); all myeloproliferative disorders (MPD), including chronic myelogenous leukemia (CML), polycythemia vera, essential thrombocythemia, and idiopathic myelofibrosis; all myelodysplastic syndromes (MDS) and myelodysplastic/myeloproliferative diseases; all acute lymphoblastic leukemias (ALL), including precursor B-lymphoblastic leukemia/lymphoma and precursor T lymphoblastic leukemia/lymphoma; chronic lymphocytic leukemia (CCL); multiple myeloma (MM); monoclonal gammopathy of undetermined significance (MGUS); amyloidosis; Hodgkin lymphoma (HL), including all classical Hodgkin lymphoma cell types (e.g., Reed Sternberg cell; including nodular sclerosis, mixed cellularity and lymphocyte depleted types); all non-Hodgkin's lymphomas (NHL) including all B cell, all T cell and all NK cell types; histiocytic disorders and mastocytosis.

From the foregoing, it should be appreciated that the patient sample can be from any tissue that can harbor a solid tumor or a non-solid tumor characteristic of an Rb protein-mediated cancer. Solid tumors that may be a source of a patient sample in any aspects of the present invention include those found in all non-hematopoietic sites, including, but not limited to lung, breast, colon and entire gastrointestinal tract, prostate, brain, pancreas, and skin. The analysis of non-solid tumors, e.g., lymphomas, leukemias, and plasma cell neoplasms, according to the present invention, involves the analysis of patient tissues that include all hematopoietic organs, without limitation, blood, lymph nodes, tonsil, spleen, thymus, and bone marrow.

According to one embodiment for diagnosing the presence of the Rb protein-mediated cancer or pre-cancerous condition, this method is carried out on a patient sample as an initial diagnostic test, where the presence of pS-Rb positive cells indicates that at least some of a patient's cells have entered a proliferative stage, which is indicative of cancer or a pre-cancerous condition.

According to another embodiment of the diagnostic procedure, the method can be repeated upon a second patient sample obtained (from the same patient) following a time delay. By comparing the results obtained on the first and second samples, a determination can be made as to whether there exists a change in the percentage of cells that are recognized by the antibody to the pS-Rb protein. An increase in the percentage of pS-Rb positive cells in the second sample indicates both the presence and the advancement of an Rb-mediated cancerous or pre-cancerous condition and/or prognosticates increased aggressiveness. Using this embodiment, the status of a known or suspected cancerous condition can be assessed, and the progression of a pre-cancerous or cancerous condition can be monitored.

The above embodiments can also include a further step of exposing the patient sample(s) to an antibody that recognizes a nuclear "marker" correlated with a specific cell-cycle stage. The proportion of cells of a given cell type that also stain for the presence of the specific cell-cycle protein is determined. Suitable antibodies are those that recognize cell-cycle proteins known to be associated with a particular phase of the cell-cycle progression described herein above. Exemplary antibodies for this aspect of the present invention include, without limitation, an antibody to Ki-67, and an antibody to skp-2. Ki-67 is a nuclear protein marker for all cycling cells but is dramatically up-regulated in G2/M cell-cycle phase. skp-2 is a marker for cells in the S phase. The patient sample(s) can be exposed to one or more cell-cycle marker antibodies in a single assay. The exposure of the patient sample to the antibody for cell-cycle markers may be simultaneous with the exposure to the pS-Rb-detecting antibody, or it may occur separately from (i.e., either before or after) the exposure to the pS-Rb antibody. This embodiment can be performed on multiple samples.

In another embodiment of the present invention, exposure to the pS-Rb antibody and a nuclear cell-cycle marker antibody are performed on a patient sample on at least two occasions, with a time delay between the at least two occasions, and it is determined whether there exists, following the time delay, an increase in the percentage of cells in the patient sample that are identified as being recognized by one or more antibodies, from time one to time two, where an increase indicates the presence or progression of an Rb-mediated cancerous or pre-cancerous condition. Using this embodiment, the status of a known or suspected cancerous condition can be assessed, and the progression of a pre-cancerous or cancerous condition can be monitored. Suitable antibodies for pS-Rb and cell cycle markers are as described above.

Solid tumors contain a substantially homogenous population of cells, therefore, staining for cell-lineage is not required in the analyses described herein. However, unlike the pure tumor cell populations in solid organ cancers, "liquid" cancers (e.g., lymphomas, leukemias, and plasma cell neoplasms) often are admixed with non-neoplastic cells. For example, in bone marrow cancers such as multiple myeloma, the cancer cells are interspersed with non-neoplastic white and red blood cell precursors. Thus, biopsies of hematopoietic tissue (e.g. bone marrow, peripheral blood, lymph node, spleen, and thymus) typically contain several cell types in addition to the malignant cells. In order to exclude interspersed non-neoplastic cells from the cell cycle analysis, double or multiple immunostaining is carried out, see e.g., FIG. 3. Each immunohistochemical reaction is carried out with a unique chromogen, on a single slide to assess the presence of cell cycle proteins in the tumor population only, excluding the non-cancerous cells from the analysis. Therefore, immunohistochemical analysis will be performed for each of several cell cycle regulatory proteins in conjunction with a tumor-specific antibody in each slide (e.g. CD20 in B cell Lymphomas, CD138 in multiple myeloma, CD68 in acute myelogenous leukemia). After the diagnosis of cancer is established by conventional microscopy and immunophenotyping, an appropriate tumor-specific antigen is selected. Therefore, another embodiment of the diagnostic procedure further includes, in addition to any of the above-described procedures, exposing the patient sample to an antibody that recognizes a cell surface marker for the neoplastic cells. In this embodiment, recognition of pS-Rb in the cells of the patient sample determines the presence of an Rb-mediated cancerous or pre-cancerous condition, and recognition the cell surface marker distinguishes the neoplastic cells from the non-neoplastic cells in the fixed sample. Thus, immunohistochemistry is performed with a cell cycle antibody (e.g. pS-Rb and/or Ki-67) and a unique chromogen, for each Ab, then immunohistochemistry is performed on the same histologic section with one or more antibodies to cell surface marker and a distinct chromogen for each cell surface marker antibody. The negative cells (i.e., those cells not recognized by pS-Rb, Ki-67 or neoplastic antibody) are counterstained. The cell surface marker antibody identifies a lineage specific protein expressed by the neoplastic cells and not expressed by the benign background cells. The percentage of cell cycle molecule-positive cancer cells is typically estimated or calculated by counts of 150 tumor cells in each of 3 separate areas of the tumor. In biopsies with uniform staining, the percentage of tumor cells expressing a certain cell cycle molecule can be estimated, obviating the need for counting cells. An exemplary assessment of the outcome for this double-staining immunohistochemistry is as follows: 0-5% of cells positive for both cell cycle protein and a neoplastic cell surface marker indicates an indolent neoplasm or no cancer present; 5-20% positive cells indicates an intermediate stage of cancer; >20% positive is indicative of an aggressive disease. The antibodies suitable for use in the present invention to detect lineage specific cells include, without limitation, those described in Table I, below.

TABLE I

| Cell Lineage | Cell Surface Marker | Source |
|---|---|---|
| B cell lymphomas, popcorn cell of nodular lymphocyte predominant Hodkin lymphoma | CD20 | Dako (Glostrup, Denmark) |
| T cell lymphomas | CD3 | Lab Vision Corporation (Fremont, CA) |
| Plasma cell neoplasms | immunoglobulin κ light chain, immunoglobulin λ light chain, | Dako (Glostrup, Denmark) |
| Plasma cell neoplasms | CD138 | Serotec (Raleigh, NC) |
| Reed-Sternberg (classical) cells in Hodgkin's lymphoma | CD30 | Dako (Glostrup, Denmark) |
| (AML or CML) Plasma cells neoplasms in extramedullary sites | CD31 | (Dako Glostrup, Denmark) |
| Myeloid (B cell) leukemias | CD43 | Becton-Dickinson (San Jose, CA) |
| Myeloid leukemia or multiple myeloma | CD56 | Novocastra (Peterborough, UK) |
| Myeloid leukemia | CD68 | Dako (Glostrup, Denmark) |
| Acute myelogenous leukemia (myeloid or mast cells) | CD117 | Dako (Glostrup, Denmark) |
| Acute lymphoblastic or myelogenous leukemia (B, T, or myeloid cells) | CD34 | Biogenex (San Ramon, CA) |

Another aspect of the present invention relates to a method of assessing the efficacy of cancer therapy for an Rb protein-mediated cancer. Basically, the analysis of any of the above diagnostic embodiments can be performed on multiple (two or more) samples from the same patient, where samples are taken before and after the administration of cancer therapy to the patient. A change in the percentage of cells identified as recognized by the pS-Rb antibody before and after cancer therapy indicates the efficacy (i.e, the ability to produce the intended result) of the cancer therapy. If the percentage of pS-Rb identified cells has increased over the course of therapy, the patient's treatment regimen warrants review and reassessment. If the percentage of pS-Rb identified cells has decreased over the course of therapy, the treatment is at least partially effective.

Another embodiment of assessing the efficacy of cancer therapy for a retinoblastoma protein (Rb)-mediated cancer involves using both the antibody that recognizes phosphorylation of a serine residue on the retinoblastoma protein (pSRb) and an antibody that recognizes a nuclear marker for a specific cell cycle-stage or stages that the proliferative cells have entered, e.g., an antibody to Ki-67 or an antibody to skp-2, as described above. A change in the percentage of identified cells recognized by the antibody to pS-Rb and/or by an antibody to a cell-cycle marker indicates the efficacy of the cancer therapy. Rb phosphorylation means the cell has crossed the mid-G1 restriction point. Ki-67 is less specific because it is catabolized so slowly; Ki-67 expression increases throughout G2 and M. However, since the Ki-67 half life is up to 24 hours, cells that immediately reenter the cell cycle still have some Ki-67 left over, even in G1. Cells that have recently exited the cell cycle will retain some (diminishing amount) of Ki-67 in the beginning of G0. Moreover, in conjunction with the relative size of the nucleus, with Ki-67, one can tell which phase of the cycle a cell is in by the pattern (it is nucleolar in S phase, granular/nuclear in G1 and solid/nuclear in M and G2). Exposure to the pS-Rb antibody and the cell-cycle marker antibodies may be simultaneous or sequential, as described above.

There are three facets to determining cancer treatment efficacy. Firstly, if the percent of pSRb positive cells shows a decrease in the second (post-therapy) patient sample relative to the pre-therapy sample, it is determined that the cancer treatment has retarded the proliferation of the pre-cancerous or cancerous cells, or has killed the cells that were proliferating. If the percent of pS-Rb positive cells remains the same, or is higher in the post-therapy patient sample than the pre-therapy sample, the therapy has either been ineffective or killed the non-proliferative fraction. If there is still a considerable percentage of the cells in the sample that are proliferating, it will not be long before the tumor load is back up to the pre-treatment level, in which case the clinician would look at the possibilities (as regards available therapy) and change the drug regimen.

Second, if the cancer drug the patient received is purported to work by a specific mechanism, the patient sample is stained to assess the efficacy with regard to that particular mechanism in the patient cells. For example, if the cancer treatment includes a drug that is supposed to retard proliferation by increasing the negative cell cycle regulator p21 (a Cdk inhibitor), double staining is carried out to compare the percent of PCs that are p21+ before vs. during therapy. If, as assessed in a patient sample, the percent of $pSRb^+$ cells is decreased and the percent of p21+ cells has increased, the conclusion is that the drug is working as it should and the patient should continue treatment with that drug (depending upon tolerance of side effects). If the percent of pSRb+ cells has increased and the percent of p21+ cells has increased, then it is concluded that the drug is working so far as the mechanism, but that the tumor cells must have some way of circumventing the effects of an increase in p21. Thus, the other CdkIs may have decreased, or the cyclins or Cdks may have increased. The mechanism involved in this particular patient's cells would then be further assessed as described above. If, for example, the p21 has increased as predicted but so has the Cdk6 (while the other CC molecules have not changed), adding a Cdk6-inhibitor to the regimen would be an appropriate recommendation. Following a short delay (e.g., a few weeks), another biopsy can be taken, and the analysis for cell cycle regulators reassessed, and a determination can then be made as to the mechanism(s) involved in this patient's disease. The process is an iterative one, based on all knowledge available to the treating physician, including knowledge gained via practice of the present invention. A therapeutic regimen is recommended based on the results of the analyses carried out as described herein above.

Lastly, when the cell cycle progression is halted with a drug, the patient may enter the plateau phase, where the cells have become stagnant, but do not die. It is possible to remain in the plateau-phase for a long period of time, for example, a patient can have a decade of good-quality life in this phase. Although the tumor load remains in the plateau phase, its effects are indolent as long as the tumor load does not increase. It is possible, however, that if other drugs are selected for treating the patient at this stage, that not only will the cell cycle progression be halted, the cells will enter apoptosis and the patient will go into a true remission.

Therefore, the method of determining cancer treatment efficacy described above can further include a step(s) of (i) exposing the patient sample(s) to one or more antibodies that recognize positive cell cycle regulators, (ii) exposing the patient sample(s) to one or more antibodies that recognize negative cell cycle regulators, (iii) exposing the patient samples(s) to an antibody that recognizes a cell surface marker for neoplastic cells, or a combination thereof, preferably including (i) and/or (ii), and (iii). The efficacy of cancer therapy is evaluated based on the determination of whether pS-Rb positive cells in the patient sample are also recognized by one or more of the positive or negative cell cycle regulators, one or more cell surface markers for neoplastic cells, or both.

Suitable pS-Rb antibodies, neoplastic cell marker antibodies, positive cell cycle regulator antibodies, and negative cell cycle regulator antibodies include those listed above, or herein after.

As described herein above and in the Examples, below, it is the balance between positive and negative cell cycle regulators that is important in the selective inactivation of Rb and the subsequent expansion of self-renewing cancers cells, which leads to disease progression through uncontrolled cell proliferation. Because multiple genetic bases exist for the mechanism(s) causing disease progression, and the genetic basis is believed to be relevant to efficacy of therapeutic regimen, another aspect of the present invention is a method of determining the mechanism of cell cycle progression in a pS-Rb positive patient sample. This method is intended to be used alone or in combination with other methods of the present invention. This method involves exposing the patient sample to an antibody that recognizes phosphorylation of serine on the retinoblastoma protein (pS-Rb) and one or more antibodies that recognize positive or negative cell cycle regulators. Cells in the patient sample that are recognized by the various antibodies are then identified. Recognition by the anti-pS-Rb antibody indicates that the cells that have passed the midpoint of G1 phase of the cell cycle. Cells in the patient sample that are recognized by the anti-pS-Rb antibody and by one or more of the positive or negative cell cycle regulators determines the mechanism of cell cycle progression of pS-Rb positive cells in the patient sample.

Antibodies to any suitable positive cell cycle regulator can be employed. Exemplary positive cell cycle regulators include, without limitation, cyclin D1, cyclin D2, cyclin D3, cyclin E, cdk4, cdk6, mcm2, and mcm7.

Antibodies to any suitable negative cell cycle regulator can be employed. Exemplary negative cell cycle regulators of the present invention include, without limitation, p16, p18, p19, p21, p27.

An exemplary list of antibodies and sources thereof for the identification of the cell cycle regulators is provided in Table II below.

TABLE II

| Protein Recognized | Source |
|---|---|
| Positive CC Regulators | |
| cyclin D1 | Lab Vision Corporation (Fremont, CA) |
| cyclin D1, cyclin D3, cyclin E | Novocastra (Peterborough, UK) |
| cyclin D2 | Santa Cruz (Santa Cruz, CA) |
| cdk4 | Cell Signaling Technology Inc. (Beverly, MA) |
| cdk6 | Cell Signaling Technology Inc. (Beverly, MA) |
| Negative CC Regulators | |
| p16, p19 | Novocastra (Peterborough, UK) |
| p18 | Santa Cruz (Santa Cruz, CA) |
| p21, p27 | Becton-Dickinson (San Jose, CA) |
| Cell Cycle Marker Proteins | |
| mcm2 | Lab Vision (Fremont, CA) |
| mcm7 | Lab Vision (Fremont, CA) |
| Skp-2 | Zymed (South San Francisco, CA) |
| Ki-67 | Zymed (South San Francisco, CA) |
| phospho-Rb | Cell Signaling Technology Inc (Beverly, MA) |

This list is not meant in any way to limit the source of suitable antibodies. Other sources for these antibodies, and other antibodies known to those in the art (or which are developed that are specific for the cell cycle regulators listed above) are also suitable in this and all embodiments of the present invention. "Specific for" as used herein means an antibody recognizes the antigen by binding to the antigen or an antigenic epitope, or fragment thereof, under suitable conditions, which are well-known in the art.

Like the other diagnostic methods of the present invention, determining the genetic mechanism of cell cycle progression involves the performance of immunohistochemistry by routine methodology on fixed, embedded tissue after antigen retrieval; and is suitable for all samples types and all cancerous or precancerous conditions listed above. Antibody immunostaining for each cell cycle regulator of interest is carried as described as described above. The percentage of tumor cells expressing the molecule of interest is then either estimated, or computed by a manual 500 tumor cell count or automated image analysis (e.g., Applied Imaging, Santa Clara, Calif.). Single staining is suitable for solid tumors. For non-solid tumors, exposure to neoplasm-lineage-specific antibodies, as described above, are useful in this aspect as well.

Another aspect of the present invention relates to a method of identifying a cell predisposed to developing a retinoblastoma protein (Rb)-mediated cancerous condition. This method involves exposing the sample to an antibody that recognizes phosphorylation of serine on the retinoblastoma protein (pS-Rb) and an antibody that recognizes a cell cycle marker, e.g., Ki-67 and skp-2. The cells in the sample that are recognized by the anti-pS-Rb antibody and the antibody to the cell cycle marker are then identified. If even a few cells positive for both (i) pS-Rb expression and (ii) Ki-67 or skp-2 expression (i.e., suspect cells) are identified, this method further involves exposing the patient cell sample to one or more antibodies that recognize negative cell cycle regulators. Low or undetectable expression of the negative cell cycle regulators in the suspect cells indicates the predisposition of suspect cells to becoming cancerous. Suitable pS-Rb antibodies, cell cycle marker antibodies, and negative cell cycle regulator antibodies include those listed above.

Another aspect of the present invention relates to a method of assessing the state of cell cycle progression in a cancer patient having a retinoblastoma protein (Rb)-mediated cancer. This method involves exposing the patient sample to an antibody that recognizes a phosphorylation of serine on the retinoblastoma protein (pS-Rb), one or more antibodies that recognize positive cell cycle regulators, and an antibody that recognizes a cell surface marker for neoplastic cells. It is then determined whether cells in the patient sample that are recognized by the anti-pS-Rb antibody are also recognized by one or more of the positive cell cycle regulators, one or more cell surface markers for neoplastic cells, or both. This allows for an assessment of the progression in the cancer patient. For example, a patient sample can be identified as positive for pS-Rb and for the presence of a positive cell cycle regulator, indicating the presence of a cancerous condition. In a solid tumor biopsy, this may provide the clinician sufficient information regarding the patient's stage of disease to make a treatment recommendation. If the cancer is of a hematopoietic tissue, the sample can be further exposed to an antibody for a neoplastic cell surface marker, thereby providing additional information regarding the type and stage of cancer. For example, for a known or suspected multiple myeloma, multiple immunostaining carried out on a BM sample biopsy would preferably include antibodies specific for pS-Rb, cyclin D1, Cdk4 and CD138; or more preferably a combination including pS-Rb, cyclin D2, Cdk6, and CD138. Other suitable pS-Rb antibodies, positive cell cycle regulator antibodies, and neoplastic cell marker antibodies, including those described above, can also be employed.

EXAMPLES

Example 1

Bone Marrow Specimen Procurement

Bone marrow specimens were obtained from volunteers without hematological disease at the Hospital for Special Surgery and from MM patients at the New York-Presbyterian Hospital under informed consent as part of an Institutional Review Board approved study. The posterior and superior iliac spines were identified before beginning the procedure. The patient was placed in a ventral or lateral decubitus position. The field was cleaned with Betadine and the area of interest was anesthetized with 1% Lidocaine. A bone marrow aspirate and biopsy was performed unilaterally using a modified Jamshidi bone marrow aspiration/biopsy needle, 11 gauge×4 inch. Several 5-7 cc aspirates were obtained by relocating the needle in each aspirate to obtain a total of approximately 30 cc of marrow. The core biopsy was then obtained. The bone marrow core biopsies were fixed in 10% neutral-buffered formalin and paraffin-embedded. $CD138^+$ normal and malignant plasma cells (greater than 90% pure) were isolated from live monolayer bone marrow aspirates using an automated MACS CD138 MicroBeads system (Miltenyi Biotechnology, Auburn, Calif.) according to the manufacturer's specifications.

Example 2

Immunohistochemistry

Plasma cells were identified with an anti-CD138 antibody and a detection system yielding a red membranous signal. To ensure that hematopoietic background cells did not express CD138 and that all plasma cells in the samples did express CD138, and to ensure that any background non-neoplastic plasma cells were not included in the analysis, the CD138 stained slides in all biopsies were compared to serial sections immunostained for cytoplasmic immunoglobulin expression (IgM, IgD, IgG, IgA, Igic or IgX); these slides were also compared to routine hematoxylin and eosin stained serial sections. The concordance between routine histologic examination, monotypic patient-myeloma isotype specific cytoplasmic immunoglobulin expression, and CD138 expression was very high; rare myeloma specimens showed weak CD138 expression in minor subpopulations of cells but none of the myeloma specimens was negative for CD138. CD138 negative plasma cells were very rare. Non-neoplastic background plasma cells were rare in all MM biopsies.

Figure 2:
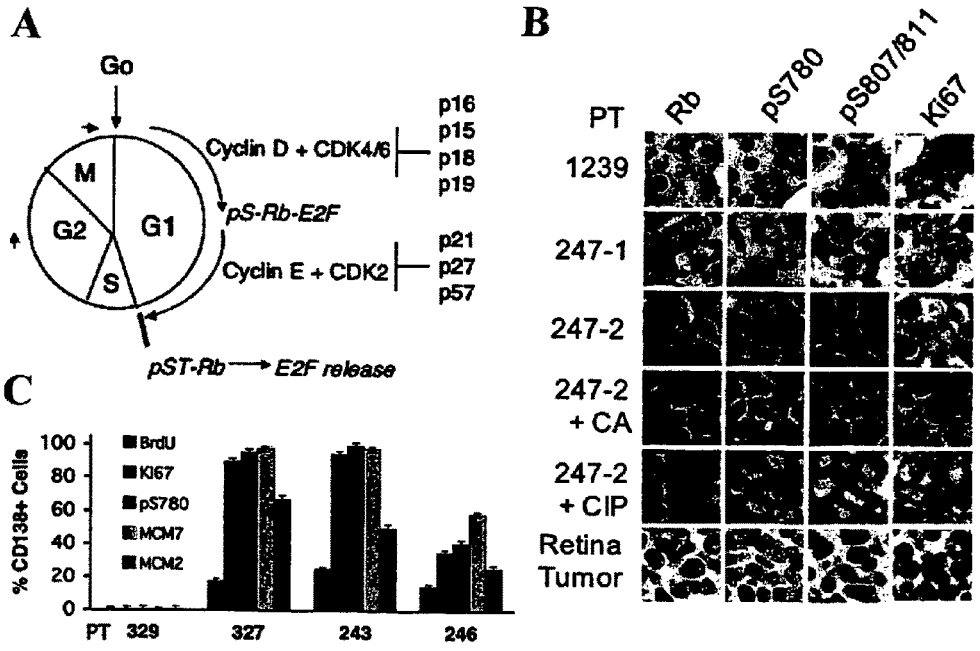
FIGS. 2A-C demonstrate that cell cycle analysis by two color immunohistochemistry is specific for detection of serine phosphorylated retinoblastoma protein (pS-Rb) in plasma cells.
Figure 6:
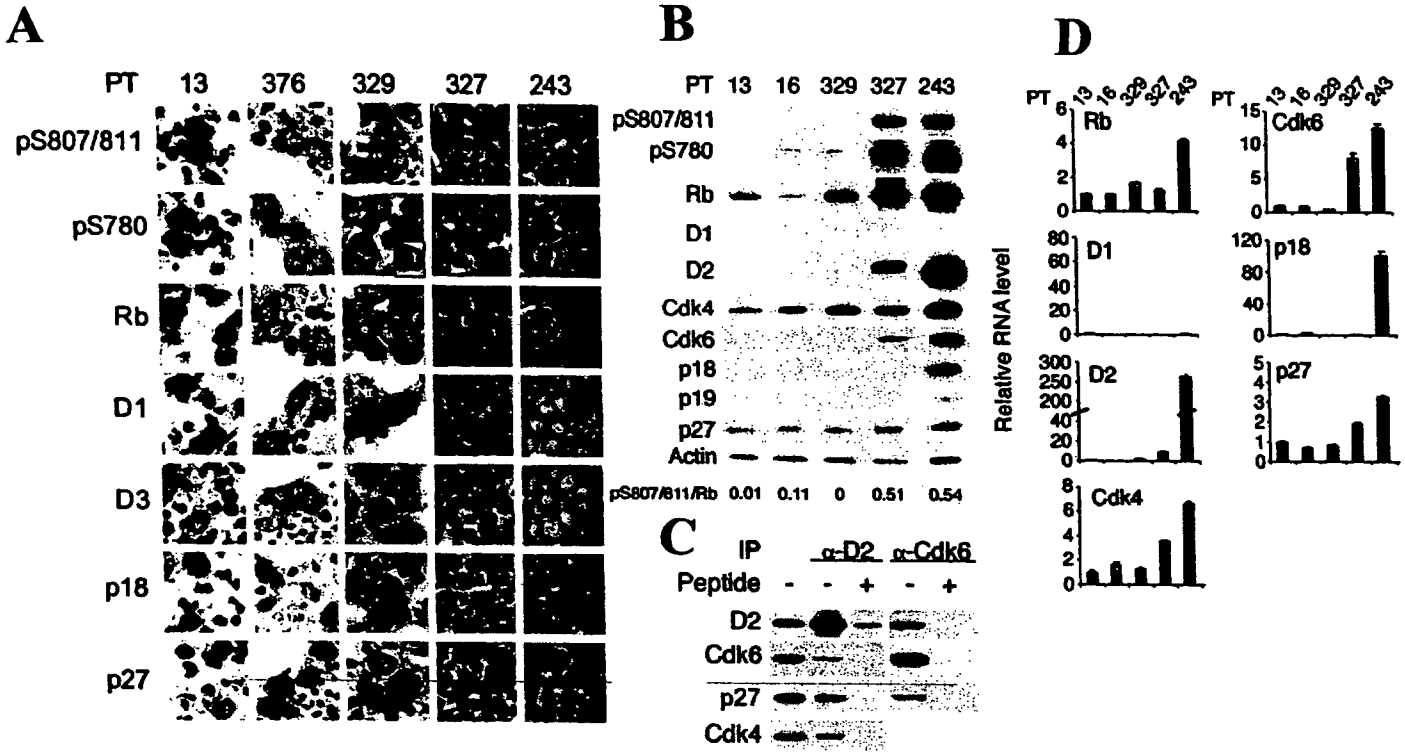
FIGS. 6A-D shows that the phosphorylation of Rb by cyclin D2-Cdk6 increases with MM progression.

Double IHC was performed to detect cell cycle molecules in situ in plasma cells and exclude other cell types from the analysis. Each slide was stained for CD138 (above) using a red chromogen, and for a cell cycle molecule with a brown chromogen; the cell cycle molecules are all nuclear with the exception of p18, which was both nuclear and cytoplasmic in most cases; and p27, which was exclusively nuclear is most cases, but nuclear and cytoplasmic in some cases. The slides were counter stained with hematoxylin (blue). Double staining thus yielded plasma cells with a red membranous signal and either a brown nuclear signal (positive for the cell cycle molecule in question), or a blue nuclear signal (negative for the cell cycle molecule in question) (FIGS. 1, 2, and 6).

To compute the percentage of plasma cells expressing a cell cycle molecule, the slides were first scanned for uniformity of staining. One hundred and fifty red CD138-membrane-positive PCs were then counted, each PC scored as either positive (containing a brown nuclear signal), or negative (containing a blue counter stained nucleus). The counts were performed in triplicate. Expression of cell cycle molecules was uniform throughout the plasma cell population in most biopsies; in the rare biopsies that showed focal expression of a protein, the counts were performed in selected areas so as to best represent overall expression in the plasma cell population as a whole (FIG. 6A, rows 4 and 5). The intensity of positive staining was scored in comparison to expression in B cells from serial sections of a single tonsil or appropriate control slide, run in parallel with the marrow slides. The following cell types were used as positive controls for these respective proteins:

Germinal center B cells: Rb, phospho-Rb, p18, Ki-67

Naive B cells/mantle zone cells: p27

Basilar squamous epithelial cells: cyclin D3

Mantle cell lymphoma, primary sample with t(11; 14): cyclin D1

For each marker, expression was recorded as I+ (fainter than control), 2+ (equal to control), or 3+ (stronger than control).

Immunohistochemistry was performed on 4 mm sections of paraffin-embedded bone marrow tissues using a TechMate500™ BioTek automated immunostainer and reagents (Ventana Medical Systems, Tucson, Ariz.). CD138$^{+}$ PC were detected using an anti-CD138 mouse monoclonal antibody (Mab) (Serotec, Raleigh, N.C.) and a red chromogen. The nuclei were visualized by counterstaining with hematoxylin (blue). Simultaneous expression of other proteins was detected with monoclonal antibodies to Ki-67, cyclin D1, MCM2, MCM7, cyclin D3, p18, p27, Rb and Cdk6 and polyclonal rabbit antisera to either pSer807/811 or pSer780 of human Rb, see Table III, below. Tissue sections were pretreated with calyculin A (Cell Signaling Technology, Inc., Beverly, Mass.) to prevent dephosphorylation during or after antigen retrieval, or with calf intestine phosphatase (Cell Signaling Technology, Inc., Beverly, Mass.) to verify phosphorylation. As a control for immunoglobulin synthesis, serial sections were stained with rabbit antibodies for IgM, IgD, IgG, IgA, Igκ and Igλ); (Dako, Glostrup, Denmark). The frequency of CD138+ cells expressing a specific protein was scored by counting 150 cells, in three areas. As positive controls, parallel analysis was performed on tissue sections containing centroblasts (Rb, phospho-Rb, p18, Ki-67); mantle zone B cells (p27); supra-basal squamous epithelial cells (cyclin D3) and mantle cell lymphoma with t(11; 14) (cyclin D1) (Sailer et al., "Prognostic Relevance of a Histologic Classification System Applied in Bone Marrow Biopsies from Patients with Multiple Myeloma: a Histopathological Evaluation of Biopsies from 153 Untreated Patients," Eur J Haematol 54(3):137-46 (1995); Ely et al., "Telomerase Activity in B-Cell Non-Hodgkin Lymphoma," Cancer 89(2):445-52 (2000), which are hereby incorporated by reference in their entirety). Correlations between D1 and D3 with Ki-67 were assessed by the t test and p values using SPSS for Windows (release 11.0, SPSS, Inc., Chicago, Ill.). p-values less than 0.05 were considered statistically significant.

TABLE III

| Patient Biopsy Data | | | | | | | | | | |
|---|---|---|---|---|---|---|---|---|---|---|
| | | | | | | | | | FISH | |
| PT | Age | Dx | Stage | Ki-67 | Bone Lesions | Ig Isotype | Tx | Karyotype | t(11; 14) t(4; 14) % Pos. | del(13q14.3) del(17p13.1) % Pos. |
| 1239 | 77 | normal | na | 0% | 0 | na | N | nl | N | N |
| 13 | 83 | normal | na | 0% | 0 | na | N | nd | nd | nd |
| 16 | 55 | MGUS | 0 | 0% | 0 | Gκ | N | nd | nd | nd |
| 376 | 77 | MGUS | 0 | 0% | 0 | Gλ | N | nd | nd | nd |
| 329 | 75 | MM | I | 0% | 0 | Aκ | N | nl | N | N |
| 336 | 62 | MM | I | 1% | 0 | Aκ | N | nd | nd | nd |
| 346 | 71 | MM | I | 0% | 0 | Gκ | N | nl | N | 13q 9% |
| 137-1 | 43 | MM | I | 0% | 0 | $\lambda^{a}$ | N | nl | N | N |
| 247-1 | 75 | MM | I | 0% | 0 | $k^{a}$ | N | nl | N | N |
| 3655 | 64 | MM | I | 0% | 0 | Gλ | N | nl | N | N |
| 254 | 71 | MM | I | 1% | 0 | Gκ | N | Complex | t(11; 14)58% | N |
| 137-2 | 44 | MM | II | 6% | 0 | $\lambda^{a}$ | N | nl | N | N |
| 247-2 | 78 | MM | II | 42% | 0 | $k^{a}$ | Y | nl | N | N |

TABLE III-continued

| Patient Biopsy Data | | | | | | | | | | |
|---|---|---|---|---|---|---|---|---|---|---|
| | | | | | | | | | FISH | |
| PT | Age | Dx | Stage | Ki-67 | Bone Lesions | Ig Isotype | Tx | Karyotype | t(11; 14) t(4; 14) % Pos. | del(13q14.3) del(17p13.1) % Pos. |
| 246 | 67 | MM | III | 35% | >2 | Aκ | Y | nd | nd | nd |
| 338 | 71 | MM | III | 0% | >2 | Gκ | N | nl | t(11; 14)25% | N |
| 282 | 55 | MM | III | 0% | >2 | λ[a] | Y | Polyploid | N | N |
| 327 | 64 | MM | III | 95% | >2 | Aκ | N | Complex | t(4; 14)88% | 13q 68% |
| 243 | 53 | MM | III | 99% | >2 | Aκ | Y | Complex | t(4; 14)75% | 13q 85% |

PT, patient number;
Dx, diagnosis;
Ig, Immunoglobulin,
[a]denotes absence of heavy chains;
Tx, Treatment;
Y, yes;
t( ), translocation;
del, deletion;
na, not applicable;
N, negative;
nl, normal;
nd, not done;
MGUS, monoclonal gammopathy of undetermined significance;
MM, multiple myeloma;
Stage, extent of disease according to Salmon Durie criteria (Durie, B. "Staging and Kinetics of Multiple Myeloma," Semin Oncol 13: 300-9 (1986), which is hereby incorporated by reference).

Example 3

Analysis of BrdU-Uptake

BrdU uptake in primary bone marrow CD138$^+$ plasma cells ex vivo was detected by immunofluorescence staining (Morse et al., "Induction of Cell Cycle Arrest and B Cell Terminal Differentiation by CDK Inhibitor p18(INK4c) and IL-6," Immunity 6:47-56 (1997), which is hereby incorporated by reference in its entirety), using a Mab FITC-anti-BrdU (Roche Diagnostics, Indianapolis, Ind.) and Texas red-conjugated rabbit anti-human Ig κ and λ antibodies (Southern Biotechnology). The frequency of BrdU$^+$ cells was determined by counting 250 cells in three areas.

Example 4

Immunoprecipitation and Immunoblotting

For immunoprecipitation, whole cell lysates were prepared by incubating cells in a lysis buffer containing 50 mM Tris-HCl, pH 7.4, 150 mM NaCl, 0.5% NP-40, 1 mM DTT, and proteases and phosphatase inhibitors on ice for 20 minutes. After clearing by centrifugation, cell lysates were incubated with goat anti-human Cdk4, rabbit anti-human Cdk6 or antimouse cyclin D2 (all from Santa Cruz, Santa Cruz, Calif.) for 2 hrs at 4° C. in the presence or absence of the corresponding blocking peptides. The immune complexes were collected by incubation with protein A/G agarose beads (Promega, Madison, Wis.) and centrifugation. Preparation of whole cell lysates and immunoblotting was as previously described (Huang et al., "Homeostatic Cell-Cycle Control by BLyS: Induction of Cell-Cycle Entry but not G1 /S Transition in Opposition to p18INK4c and p27Kip1," Proc Natl Acad Sci USA 101:17789-94 (2004), which is hereby incorporated by reference in its entirety), using one of the following antibodies: mouse monoclonal antibody to human Rb, Cdk6, p 18, cyclin D1 (Cell Signaling Technology, Inc., Beverly, Mass.), and human p27 and actin (BD-Pharmingen, San Diego, Calif.); and rabbit antibodies to pSer807/811 and pSer780 of human Rb (Cell Signaling Technologies, Beverly, Mass.), mouse Cdk4 (cross-reactive with human Cdk4), and human cyclin D2 (Santa Cruz, Santa Cruz, Calif.). Membranes were rinsed in TBS-T, incubated with HRP-linked goat antimouse/rabbit secondary antibodies (1:5,000) for 60 min, and developed with the SuperSignal West Femto Maximum Sensitivity Substrate (Pierce, Rockford, Ill.).

Example 5

Real Time RT-PCR

Total RNA was isolated from CD138+ cells using the TRI-zol reagent (Invitrogen, Carlsbad, Calif.), and analyzed by real time RT-PCR as previously described (Huang et al., "Homeostatic Cell-Cycle Control by BLyS: Induction of Cell-Cycle Entry but not G1/S Transition in Opposition to p18INK4c and p27Kip1," Proc Natl Acad Sci USA 101: 17789-94 (2004), which is hereby incorporated by reference in its entirety), using Assays-on-Demand gene expression mixes specific for Rb, cyclin D1, cyclin D2, Cdk4, Cdk6, p18, p27 and 18S ribosomal RNA, and the TaqMan Universal PCR Master Mix (Applied Biosystems, Foster City, Calif.). Reactions were carried out in triplicate, in the ABI PRISM 9600 Sequence Detection System. The relative amount of products was determined by the comparative Ct methods according to instructions from Applied Biosystems (Foster City, Calif.).

Example 6

Phosphorylation of Rb by Cdk4/6 Increases with Proliferation in Multiple Myeloma Progression Phosphorylation of Rb by Cdk4/6 in cooperation with one of the D cyclins promotes early G1 cell cycle progression and the release of E2F transcription factors that are necessary for S phase entry, as shown in FIG. 2A (Classon et al., "Combinatorial Roles for pRb, p 107, and p130 in E2F-

Mediated Cell Cycle Control," Proc Natl. Acad Sci USA 97:10820-5 (2000); Stevaux et al., "A Revised Picture of the E2F Transcriptional Network and Rb Function," Curr Opin Cell Biol 14:684-91 (2002), which are hereby incorporated by reference in their entirety). In situ immunohistochemical analysis of formalin fixed bone marrow (BM) sections detected no Cdk4/6-specific phosphorylation of Rb on either serine 780 (pS780) or serine 807/811(pS807/811) (Knudsen et al., "Differential Regulation of Retinoblastoma Protein Function by Specific Cdk Phosphorylation Sites," J Biol Chem 271:8313-20 (1996); Zarkowska et al., "Differential Phosphorylation of the Retinoblastoma Protein by G1 /S Cyclin-Dependent Kinases," J Biol Chem 272:12738-46 (1997), which are hereby incorporated by reference in their entirety), in normal, G13-arrested CD138$^+$ BM plasma cells (BMPCs), as shown in FIG. 2B, #1239. pS780 and pS807/811 were similarly absent in CD138$^+$ bone marrow MM cells (abbreviated as MM cells) at the time of initial MM diagnosis (#247-1), but appeared and increased prominently with cell proliferation during treatment-free progression (#247-2), as shown by Ki-67 expression, and as seen in FIG. 2B and Table III. The phosphorylation signals were confirmed, as they did not vary by protection with a phosphatase inhibitor, calyculin A, and were completely eliminated by calf intestine phosphatase, as shown in FIG. 2B, independent of the MM stage (Durie B., "Staging and Kinetics of Multiple Myeloma," Semin Oncol 13:300-9 (1986), which is hereby incorporated by reference in its entirety), or treatment history, the frequencies of MM cells expressing pS780 correlates tightly with those expressing mini-chromosome maintenance proteins MCM7 and MCM2, two components of the DNA replication complex, as shown in FIG. 2C. This linear relationship between Rb phosphorylation and DNA replication was verified by the uptake of 5-Bromo-2'-deoxyuridine (BrdU) in freshly purified MM cells ex vivo, as shown in FIG. 2C. Moreover, the frequencies of Rb phosphorylation also correlated strongly with cell proliferation based on Ki-67 expression. Thus, Cdk4/6 phosphorylation of Rb increases with DNA replication and MM cell proliferation during MM progression.

Example 7

Figure 3:
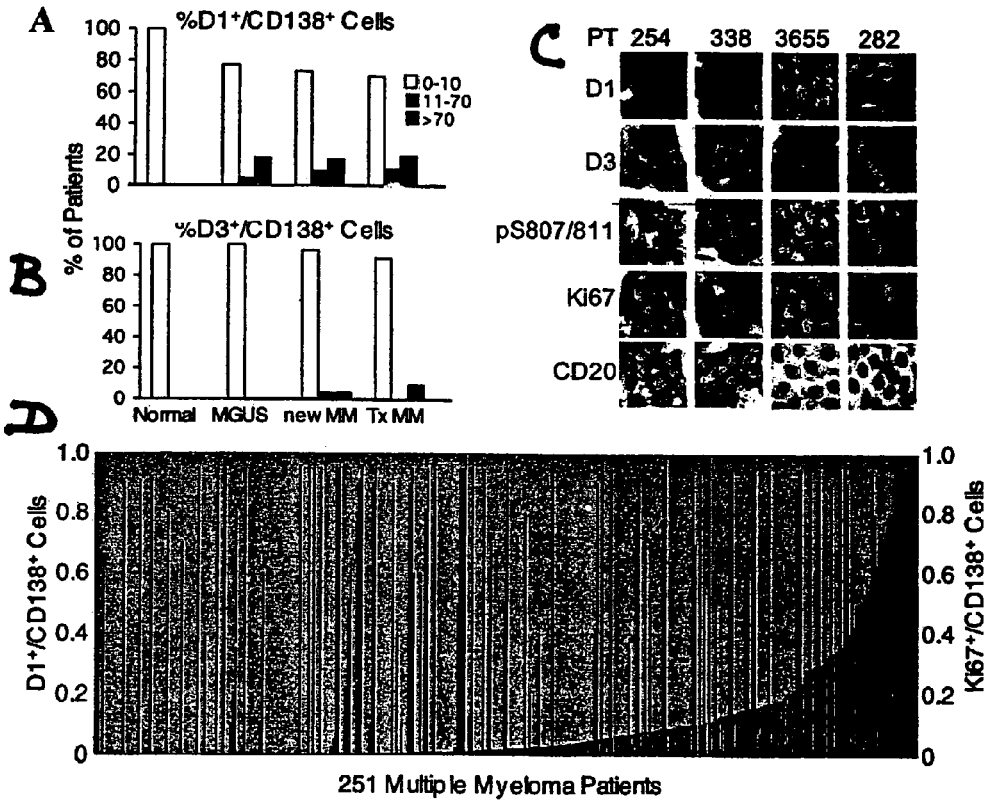
FIGS. 3A-D show that expression of cyclin D1 and D3 is mutually exclusive and not correlated with cell cycle progression.
Figure 4:
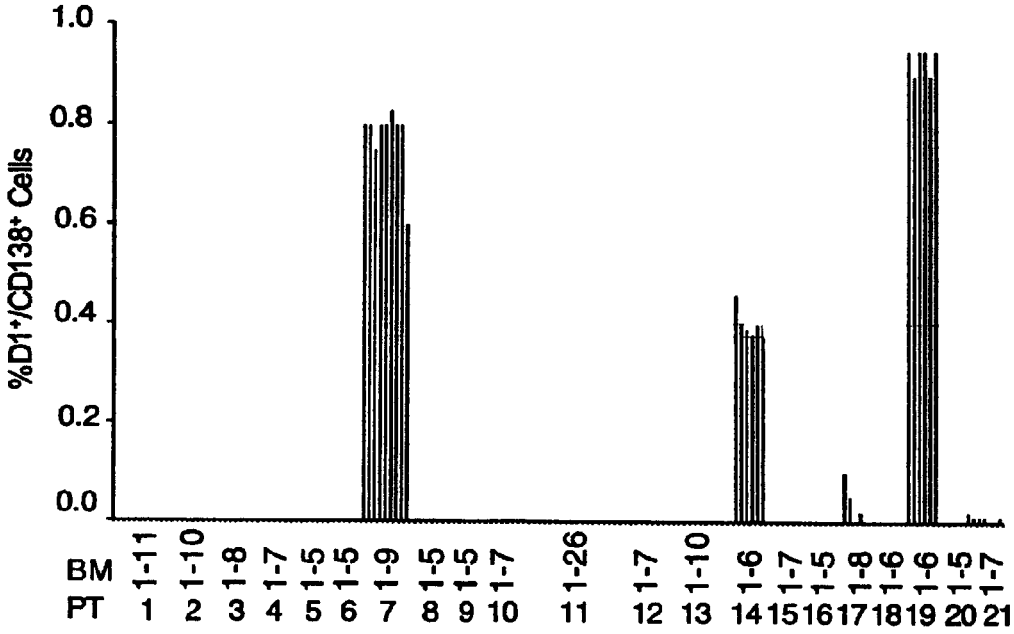
FIG. 4 is a sequential analysis of cyclin D1 expression in serial biopsies from individual MM patients. Double immunohistochemistry was performed to detect CD138 and cyclin D1. The percentage of D1+/CD138+ cells in each biopsy is plotted for 21 patients followed for an average of 72.7 months (range 31-166) with an average of 8 (range 4-26) biopsies, taken at variable intervals of time, for each patient. BM: bone marrow biopsy, PT: patient.

Expression of Cyclin D1 and Cyclin D3 is Mutually Exclusive and Insufficient to Promote Rb Phosphorylation To determine which of the D cyclins cooperates with Cdk4/6 in phosphorylating Rb in MM cells, serial sections of bone marrow biopsies from 251 mM patients were analyzed, along with 56 pre-symptomatic MGUS (Monoclonal Gammopathy of Undermined Significance) patients and 64 normal individuals. MGUS patients have monoclonal Ig detectable in their peripheral blood but are well ("precancerous") and do not meet the clinical criteria for MM. MGUS is more common than any other hematopoietic neoplasm. The occurs in 2% of patients 50-59 years old, and increases with age to 8.3% in patients over 80 (Kyle et al., "Prevalence of Monoclonal Gammopathy of Undetermined Significance (MGUS) among Olmsted County, MN Residents 50 Years of Age," Abstract #3476 Blood 102(11) (2003)). MGUS progresses to MM at a rate of 1% of patients per year (Kyle et al., "A Long-Term Study of Prognosis in Monoclonal Gammopathy of Undetermined Significance," N Engl J Med 346(8):564-9 (2002)). Cyclin D1 was not expressed in any normal individuals, but was present in more than 10% of the CD138$^+$ cells, in 23% of the MGUS patients, and in 28% of the MM patients, regardless of disease stage or treatment history, as shown in FIGS. 3A and 3B. These findings are consistent with the notion that overexpression of cyclin D1 occurs early in MM pathogenesis. The expression of cyclin D3 was less frequent (9%), and mainly in treated MM patients. In most cyclin D1- or D3-positive cases, expression was detected in greater than 70% of CD138$^+$ MM cells, as shown in FIGS. 3 and 4. Importantly, the expression of cyclin D1 and cyclin D3 was mutually exclusive and did not promote cell cycle progression, as evidenced by the lack of Cdk4/6 phosphorylation of Rb (pS807/811) and Ki-67 expression, as shown in FIG. 3C. The lack of correlations between Ki-67 and cyclin D1 expression (p value=0.878) and Ki-67 and cyclin D3 (p value=0.527) was verified by statistical analysis of all 251 mM patients, as shown in FIG. 3D. Analysis of sequential bone marrow biopsies (from 5 to 26 per patient) from an additional 21 mM patients followed for an average of 6 years (from 31 to 166 months) further revealed that cyclin D1 expression did not change during the clinical course, as shown in FIG. 4. Cyclin D1 was expressed and maintained in MM cells of four patients, at frequencies of 41% (PT #14), 75% (PT #7), 92% (PT#19), and 2% (PT#21), but not at all in the other patients. The only exception was the reduction of D1 expression from 10 to 0% of MM cells in one patient (PT#17). These longitudinal studies support the analysis of 251 patients, as seen in FIG. 3, that cyclin D1 is expressed in ~25% of MM patients and is maintained throughout the clinical course. Thus, expression of cyclin D1 and D3 in MM cells is mutually exclusive and insufficient to promote Rb phosphorylation or cell cycle progression.

Example 8

Rb is Selectively Phosphorylated by Cyclin D2-Cdk4/6 or by Cyclin D1-Cdk4 in Multiple Myeloma Cells G1 cell cycle progression and S phase entry in primary B cells are differentially regulated by physiologic signals (Huang et al., "Homeostatic Cell-Cycle Control by BLyS: Induction of Cell-Cycle Entry but not G1/S Transition in Opposition to p18INK4c and p27Kip1," Proc Natl Acad Sci USA 101:17789-94 (2004), which is hereby incorporated by reference in its entirety). The lack of correlation between cyclin D1 or D3 expression, even at high levels, and Rb phosphorylation, as shown in FIG. 3, suggests that Cdk4/6 is limiting and that cyclin D2 expression might underlie cell cycle deregulation in MM. This led to the investigation of the timing and the mechanism of Rb phosphorylation further by immunohistochemistry in parallel with immunoblotting of MM cells purified from early stage MM patients, which had limited proliferation (Ki-67 was expressed in <0.1% of MM cells, see FIGS. 5A-C and Table III). Rb was not phosphorylated in normal BMPCs due to lack of D cyclins, despite the presence of Cdk4, as shown in FIG. 5B. It was phosphorylated by cyclin D1-Cdk4 when they were coordinately increased in the absence of cyclin D2 or D3 or Cdk 6, as shown in FIGS. 5A-B, #336. In MM cells from other early stage MM patients, however, Rb was phosphorylated by cyclin D2 in cooperation with either Cdk6 or Cdk4 in the absence of cyclin D1 or D3, following coordinated elevation of cyclin D2 and Cdk6 proteins, as shown in FIGS. 5A-B #346. The mRNAs encoding cyclin D2 and Cdk6, as well as cyclin D1 and Cdk4, were correspondingly increased based on real-time RT-PCR analysis as shown in FIG. 5C. Rb, therefore, is phosphorylated by either cyclin D2-Cdk6/4 or cyclin D1-Cdk4, but not both, before the onset of significant DNA replication early in MM progression. The basis for these striking and mutually exclusive partnerships apparently lies in the exclusive expression of specific D cyclins and coordinated activation of the specific D cyclin and Cdk genes.

Example 9

Phosphorylation of Rb by Cyclin D2-Cdk6, but not by Cyclin D1-Cdk4, in Discrete Bone Marrow Foci Sequential immunohistochemical analysis early in the clinical course further revealed the emergence of discrete bone marrow foci in which MM cells expressed high levels of Cdk6, pS780, and Rb simultaneously before significant proliferation, as shown in FIG. 5A (compare 137-2 to 137-1, Table 1). Cyclin D2, although not detectable by the immunohistochemical method, is the obligatory catalytic partner for Cdk6 in the absence of cyclin D1 or D3, as shown in FIG. 5B. Phosphorylation of Rb by Cdk6-cyclin D2 in discrete focal bone lesions is in sharp contrast to the uniform expression of cyclin D1 and D3, in greater than 70% MM cells, at lower frequency in scattered MM cells, or not at all as shown in FIG. 3B. Expression of cyclin D1, but not D2 or D3, was associated with strong expression of CD20, a B cell surface protein normally present earlier in B cells, but not in differentiated plasma cells, as shown in 3B. Moreover, coordinated activation of cyclin D1 and Cdk4 RNA was accompanied by prominent increases in Rb and $p27^{Kip1}$ mRNAs and decreases in cyclin D2 and Cdk6 mRNAs as shown in FIG. 5C. $p27^{Kip1}$ is apparently subject to complex regulation in cyclin D1-Cdk4-expressing MM cells because there was no correlation between mRNA and protein expression as shown in FIG. 5C. Phosphorylation of Rb by cyclin D1-Cdk4 and by cyclin D2-Cdk6, therefore, is distinguishable by the focal Cdk6 expression and by differential gene expression early in the clinical course.

Example 10

Selective Phosphorylation by Cyclin D2-Cdk6/4 Enhanced in Advanced MM

Which of the cyclin-Cdk pairs phosphorylates Rb in MM progression and relapse was the next question investigated. Both pS780 and pS807/811 were below the level of immunohistochemical detection in CD138+ cells in MGUS patients (#376), although pS780 was appreciable by immunoblotting (#16), as shown in FIG. 6A-B and Table 1. The frequency of MM cells expressing pS780 and pS807/811 was extremely low in stage 1 (PT#329), but increased in stage III in the absence of therapy (PT#327) to levels approaching that of relapsed stage III MM (PT#243), as shown in FIG. 6A. The increase in Rb phosphorylation was confirmed by immunoblotting, as shown in FIG. 6B, and appeared unrelated to cytogenetic abnormalities (Table III). Moreover, the frequency of MM cells expressing high levels of the Rb protein rose substantially during MM progression, as shown in FIGS. 2B and 4A, and in advanced MMs, as shown in FIG. 6B. This may reflect reduced apoptosis of MM cells, considering that Rb is subject to caspase cleavage (Chau et al., "Signal-Dependent Protection from Apoptosis in Mice Expressing Caspase-Resistant Rb," Nat Cell Biol 4:757-65 (2002), which is hereby incorporated by reference in its entirety).

Despite this, the ratios between phosphorylated Rb and total Rb increased in advanced MM, shown in FIG. 6B, confirming heightened inactivation of Rb.

Cyclin D2 was copiously expressed in stage III MM cells (PT#327) and further amplified in relapsed MM cells (PT#243), concomitant with enhanced Cdk6 expression and Rb phosphorylation, as shown in FIG. 6B. Given the absence of cyclin D1 and cyclin D3 in these cells, these results correlate MM progression with selective Rb phosphorylation by cyclin D2-Cdk6. Supporting this possibility, cyclin D2 associates with Cdk6, as determined by reciprocal immunoblotting analysis of cyclin D2 and Cdk6 immune complexes, as shown in FIG. 6C. However, cyclin D2 also associates with Cdk4, despite its more modest increase in stage III MM cells (PT#327 and PT#243) from normal BMPCs (PT#13), as shown in FIGS. 6B-C. Thus, in advanced and relapsed MMs, Rb is phosphorylated primarily by cyclin D2 in cooperation with Cdk6 in concert with Cdk4.

As in early MM, as shown in FIG. 5C, the cyclin D2-Cdk6 partnership is rooted in coordinated RNA activation, whereas the regulation of Rb, Cdk4, and $p27^{Kip1}$ appeared to be more complex, as shown in FIG. 6D. Cdk6 and Cdk4 each can titrate CdkIs, by forming inactive binary complexes with early G1 CdkIs or ternary complexes with D cyclin and late G1 CdkIs (Sherr et al., "CDK Inhibitors: Positive and Negative Regulators of G1-Phase Progression," Genes Dev 13:1501-12 (1999), which is hereby incorporated by reference in its entirety). Given the correlation between Rb phosphorylation and DNA replication, as shown in FIG. 2C, and the increase in $p18^{INK4c}$ in advanced MM stages, as shown in FIGS. 6B and 6D, it appears that once cyclin D2 and Cdk6/4 in aggregate are elevated above a threshold, Rb phosphorylation ensues, and G1 to S cell cycle progression is unimpeded by the increases in CdkIs. Indeed, $p27^{Kpi1}$ was present in both cyclin D2 and Cdk6 immune complexes, as shown in FIG. 6C. On this basis, it was concluded that selective Rb phosphorylation by cyclin D2-Cdk6/4 is a consequence of coordinated activation of the cyclin D2 and Cdk6 genes and is enhanced in MM progression.

Discussion of Examples 1-10

In multiple myeloma, each case is characterized by the expression of one, and only one, cyclin D in MM cells. In these cancer cells, selective inactivation of Rb is a critical determinant of G1 cell cycle progression, reminiscent of that in normal B cells, in which Rb phosphorylation and S phase entry are subject to differential control by physiologic signals (Huang et al., "Homeostatic Cell-Cycle Control by BLyS: Induction of Cell-Cycle Entry but not G1/S Transition in Opposition to p18INK4c and p27Kip1," Proc Natl Acad Sci USA 101:17789-94 (2004), which is hereby incorporated by reference in its entirety). Overexpression of cyclin D1 or D3 rarely promotes Rb phosphorylation or G1 cell cycle progression, as seen in FIG. 3. Although Rb can be selectively inactivated by cyclin D2-Cdk6/4 or cyclin D1-Cdk4 early in MM oncogenesis, only the cyclin D2-Cdk6/4 partnership is enhanced in MM progression and correlates with cell proliferation. In the absence of protein expression or functional analysis, overexpression of cyclin D1 RNA in MM has been paradoxically linked to a more favorable prognosis (Sailer et al., "Prognostic Relevance of a Histologic Classification System Applied in Bone Marrow Biopsies from Patients with Multiple Myeloma: A Histopathological Evaluation of Biopsies from 153 Untreated Patients," Eur J Haematol 54(3):137-46 (1995); Ely et al., "Telomerase Activity in B-Cell Non-Hodgkin Lymphoma," Cancer 89(2):445-52 (2000); Fonseca et al., "Myeloma and the t(11; 14)(q13; 132); Evidence for a Biologically Defined Unique Subset of Patients, Blood 99(10):3735-41 (2002); Moreau et al., "Recurrent 14g32 Translocations Determine the Prognosis of Multiple Myeloma, Especially in Patients Receiving Intensive Chemotherapy," Blood 100:1579-83 (2002); Soverini et al., "Cyclin D1 Overexpression is a Favorable Prognostic Variable for Newly Diagnosed Multiple Myeloma Patients Treated with High-Dose Chemotherapy and Single or Double Autologous Transplantation," Blood 102:1588-94 (2003), which are all hereby incorporated by reference in their entirety). Together with the mutually exclusive expression of cyclin D1 and D2 in all MM stages, as shown in FIGS. 3-5, these data suggest that the absence of the cyclin D2-Cdk6 partnership underlies the more favorable clinical outcome in cyclin D1-expressing MMs, and that selective cyclin D2-Cdk6 partnership promotes cell cycle deregulation and MM progression.

Figure 5:
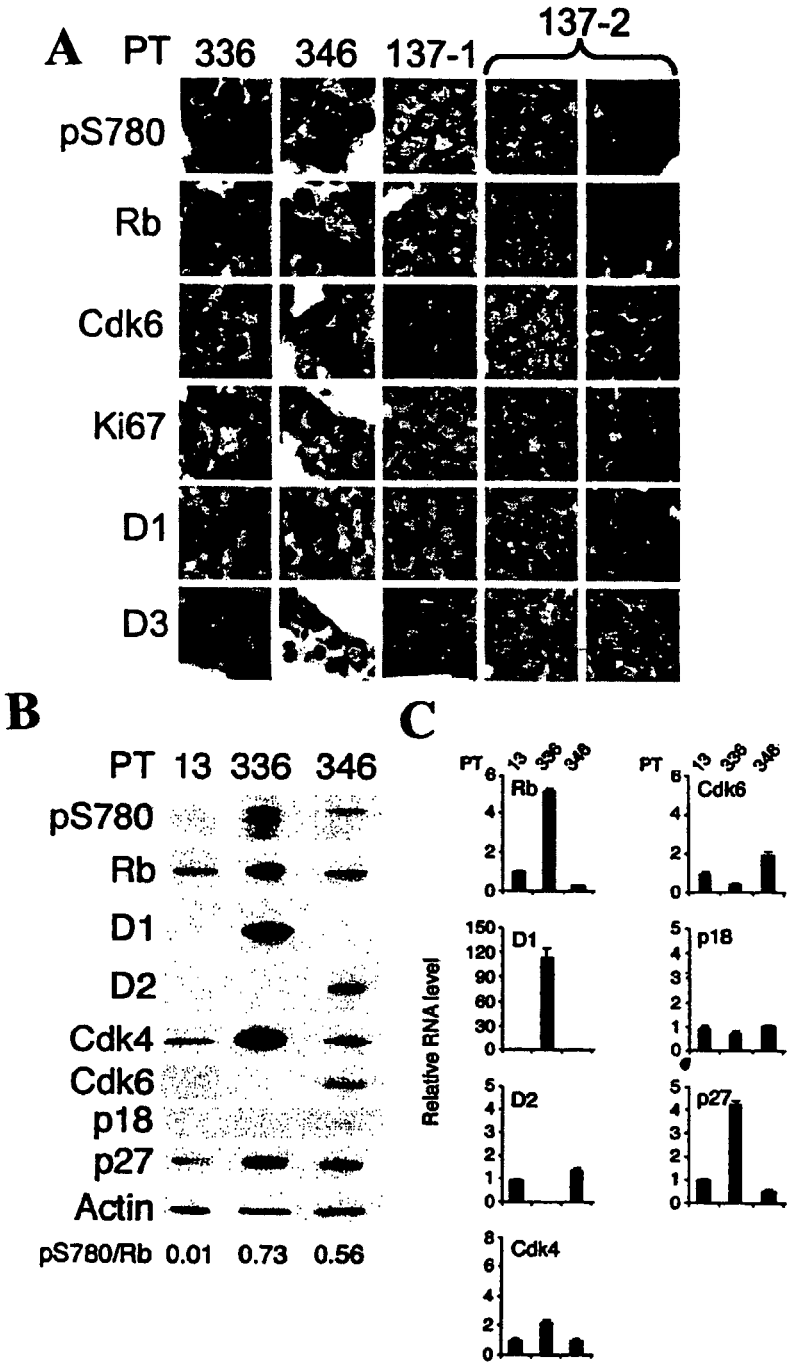
FIGS. 5A-C demonstrate the selective phosphorylation of Rb by cyclin D1-Cdk4 or cyclin D2-Cdk4/6 in untreated early stage MM patients.

Cyclin D2 and Cdk6 are not expressed in normal bone marrow plasma cells, as shown in FIG. 5. Overexpression of cyclin D2 has two functional consequences: promoting Rb phosphorylation and early G1 progression by acting as a catalytic subunit for Cdk6/4, and accelerating G1 to S cell cycle progression by removing the late G1 CdkI, $p27^{Kip1}$, as shown in FIG. 6. The latter requires that Cdk6 and Cdk4 in aggregate be in molar excess of the early G1 CdkIs such as $p18^{INK4c}$. Supporting this possibility, it was found that the coordinated increases in cyclin D2 and Cdk6 led to both Rb phosphorylation and the assembly of cyclin D2-Cdk6 complexes that contain $p27^{Kip1}$, as shown in FIGS. 6B-C. It remains to be determined whether by forming the ternary complexes, $p27^{Kip1}$ in turn stabilizes cyclin D2 and Cdk6, as is the case of cyclin D1-Cdk4 complex formation in primary mouse embryonic fibroblasts (Cheng et al., "The p21(Cip1) and p27(Kip1) CDK 'Inhibitors' are Essential Activators of Cyclin D-Dependent Kinases in Murine Fibroblasts," Embo J 18:1571-83 (1999), which is hereby incorporated by reference in its entirety). Nonetheless, differential regulation of $p27^{Kip1}$ at both RNA and protein levels in MM cells expressing cyclin D1-Cdk4 or cyclin D2-Cdk6, as shown in FIGS. 4-5, suggests that $p27^{Kip1}$ may modulate G1 progression in tandem with selective Rb phosphorylation.

The partnership between D cyclins and Cdks is determined largely by selective RNA activation, as shown in FIGS. 5A-C and FIGS. 6A-D. On this basis, it is proposed that there are two molecular subtypes of self-sustaining MM cells that are distinguishable by selective activation of D cyclins and Cdk4/6 early in MM pathogenesis and during disease progression. Deciphering the genetic alterations and the epigenetic signals that cooperate in generating and differentially maintaining these two MM subtypes poses important challenges for the immediate future. Overexpression of Cyclin D1 or D3 is associated with chromosomal translocation, as shown in FIGS. 3A-C and Table III (Shaughnessy et al., "Cyclin D3 at 6p21 is Dysregulated by Recurrent Chromosomal Translocations to Immunoglobulin Loci in Multiple Myeloma," Blood 98:217-23 (2001); Stevaux et al., "A Revised Picture of the E2F Transcriptional Network and Rb Function," Curr Opin Cell Biol 14:684-91 (2002), which are incorporated by reference in their entirety). Cyclin D2 is transactivated by the transcription factor c-Maf, which is elevated in 50% of MM cases and can promote pathologic interaction with bone stroma (Hurt et al., "Overexpression of c-maf is a Frequent Oncogenic Event in Multiple Myeloma that Promotes Proliferation and Pathological Interactions with Bone Marrow Stroma," Cancer Cells 191-9 (2004), which is incorporated by reference in its entirety). Elucidating the mechanism by which selective cooperation between D cyclins and Cdk4/6 controls early G1 cell cycle progression may also advance our understanding of cell cycle deregulation in MM oncogenesis and guide treatment selection.

Example 11

Testing IHC Methods to Assess Cell Cycle Status in MM

As shown above, IHC can be used to assess cell cycle status in vivo, in situ in routinely acquired BMBXs. With WB and real time RT-PCR on CD138-selected aspirate MM cells, these methods were validated and it was determined that the critical molecules for cell cycle progression in MM are Cdk6 and cyclin D2, both of which are regulated at the transcriptional level. The lack of proliferation among MM cells with high levels of similar cyclins (D1 or D3; FIGS. 4C and 5A) suggests that up-regulation of Cdk6 is the more critical event in disease progression.

The above data suggests that the IHC methods of the present invention are suitable for predicting the outcomes for MM patients. For example, carrying out the present invention on a BM sample using antibodies for 1) the neoplastic marker CD138, 2) positive cell cycle regulator Cdk6, 3) pSRb, and 4) the cell cycle marker Ki-67, one can assess the status of cell cycle progression at the single cell level, and make a well-reasoned prediction of outcome for that patient. For routine analysis of BM aspirates, a manual 500 cell count typically is performed.

To test the ability of these IHC methods to predict outcomes, biopsies from 4 groups of patients were acquired. For each group multivariate analysis to assess independence of IHC data will be performed.

The first group is composed of advanced stage patients who relapsed while on therapy. Biopsies were taken at the time of relapse; the patients then were started on high dose Dexamethasone (HDDex) and followed to assess clinical progression. Time to progression (TTP) while on HDDex is considered the gold standard by clinicians for assessing drug efficacy in MM. Cdk6, Ki-67 and Rb phosphorylation will be compared with TTP. In addition, other early G1 cell cycle (CC) molecules will be measured to assess which CC profiles are most sensitive and most resistant to steroids. Preliminary data, merely assessing Ki-67/CD138 on only the first 18 of 50 patients, approaches statistical significance. Cox-regression analysis revealed a 1.5 times greater likelihood of progression per unit increase in Ki-67 ($p=0.07$) (Ely et al., "Plasma Cell Proliferation Index As a Clinical Prognosticator for Relapsed Multiple Myeloma," IXth International Workshop on Myeloma, Salamanca, Spain, May 26, 2003. Hematol J 4S: 169 (2003)). The trend is expected to continue and the data to easily reach statistical significance. Because these data reflect functional biologic features, whereas serum biomarkers and performance scores only reflect the extent of disease and its downstream effects on overall health, it is expected that CC analysis will prove to be an earlier and independent prognostic variable. Also, because pSRb and Cdk6 are upstream of Ki-67, and because of the extended half-life of the Ki-67 protein, pSRb and Cdk6 are expected to be more specific and earlier indicators of a poor prognosis than even Ki-67.

The second group of patients was biopsied at the time of diagnosis with pre-symptomatic MM ("smoldering myeloma"). Results will be compared the TTP, off treatment, to symptomatic MM.

The third group is composed of patients who had biopsies taken immediately before tandem autologous stem cell transplant. CC data will be compared with survival. Because this group is currently 10 years post-transplant, the data is expected to be highly informative.

Lastly, biopsies from over 100 patients with MGUS have been analyzed, and those patients are being followed prospectively to assess whether CC IHC can predict progression to MM.

Example 12

Development of Cell Cycle-Specific Drugs

The present invention can be used for analyzing biopsies prospectively from patients undergoing treatment with experimental drugs. Using the present invention, efficacy of the drugs can be corroborated and the mechanism(s) of action elucidated. Because many anti-cancer drugs are directed at cycling cells and affect some molecules more than others, the methods described above will be suitable for determining which CC profiles are most susceptible to therapy with each agent. Although the data pinpoints Cdk6 and D2 as the most important molecules in MM progression, based on what is known about the mechanisms of these drugs, it is expected that the efficacy of some agents will depend upon other CC molecules. Along with data from steroid treatment (e.g., dexamethasone, a commonly used anti-cancer agent), this in vivo methodology may be a first step in enabling the provision of pre-treatment molecule-specific biologic data that can be used to decide which therapy is most promising for an individual patient. The model of cell cycle analysis described herein can then be applied to the analysis of other drugs, even in other types of cancer.

Multiple myeloma (MM), the second most common hematopoietic cancer in humans, ultimately becomes refractory to treatment when self-renewing MM cells begin unrestrained proliferation. The mechanism that underlies deregulated cell cycle re-entry and progression in MM was previously unknown. Herein it is shown that one, but not more than one, of the three early G1 D cyclins is elevated in MM cells. Cyclin D2 and the early G1 cyclin dependent kinase, Cdk6, are coordinately increased, which, in concert with the existing Cdk4 overrides inhibition by Cdk inhibitors, lead to phosphorylation of the retinoblastoma protein Rb. By contrast, elevation of cyclin D1 or D3 expression, even to high levels, rarely results in Rb phosphorylation or proliferation unless Cdk4 is increased in the absence of Cdk6. G1 cell cycle progression in MM, is therefore, controlled by a selective cyclin D-Cdk partnership, which is determined largely by transcriptional activation of specific D cyclin and Cdk genes. Phosphorylation of Rb by cyclin D2-Cdk6 occurs in discrete foci of bone marrow MM cells before significant proliferation early in the clinical course, and is heightened with disease progression and cell proliferation. By contrast, expression of cyclin D1 and D3 is uniform among MM cells and constant in the clinical course. Thus, selective inactivation of Rb by cyclin D2-Cdk6 phosphorylation underlies deregulated cell cycle re-entry that promotes the expansion of self-renewing MM cells and disease progression.

A close look at the literature shows that, as currently defined, MM is not a single entity. It is a group of biologically disparate diseases. The median five year survival is 31%, but up to 13% of patients survive more than 10 years (Finnish, "Long-Term Survival in Multiple Myeloma: a Finnish Leukaemia Group Study," Br J Haematol 105(4): 942-7 (1999), which is hereby incorporated by reference in its entirety). In nine identical clinical trials on stage-matched patients, the median survival ranged from 1.6 to 3.5 years, which is a vast difference for patients and their families (Bergsagel D E, "Is Aggressive Chemotherapy More Effective in the Treatment of Plasma Cell Myeloma?" Eur J Cancer Clin Oncol 25(2):159-61 (1989), which is hereby incorporated by reference in its entirety). Gene arrays also have shown that MM is a group of overlapping but biologically different cancers (Shaughnessy J Jr., "Primer on Medical Genomics. Part IX: Scientific and Clinical Applications of DNA Micro arrays—Multiple Myeloma as a Disease Model," Mayo Clin Proc 78(9): 1098-109 (2003), which is hereby incorporated by reference in its entirety). These studies show great biologic diversity within the current definition and within each clinical stage of MM. The same can be said of MGUS. If followed for 20 years, 25% of MGUS patients will progress to MM (Kyle et al., "A Long-Term Study of Prognosis in Monoclonal Gammopathy of Undetermined Significance," N Engl J Med 21; 346(8): 564-9(2002), which is hereby incorporated by reference in its entirety). However, there currently is no way to tell which patients will progress. This presents two critical problems. First, by ignoring the biologic differences between patients' MM cancers, clinicians are denied information that might help them make better treatment decisions. Second, because patients with biologically different MMs are lumped together only on the basis of stage in drug trials, it is likely that from a biologic perspective, trial data inadvertently compares apples to oranges.

The present invention uses immunohistochemistry (IHC) on BMBXs system to evaluate CC in a method that is elegant, yet simple enough for use in all hospitals for routine patient care. IHC is currently a standard adjunct for diagnosis in other cancers. Because it is performed on routinely preserved tissue, IHC can be used retrospectively. For simultaneous detection of multiple proteins, two or more antibodies can be used on a single section, each with its own unique chromogen, as shown in FIG. 1 (Tourigny et al., "CDK Inhibitor p18(INK4c) is Required for the Generation of Functional Plasma Cells," Immunity 17(2):179-89 (2002), which is hereby incorporated by reference in its entirety). IHC CC data parallel the PCLI but, in addition to the above advantages, also improve upon it by being in vivo, in situ.

Recent achievements in MM research already have improved the lives of some patients. The availability of new drugs adds urgency to the need for practical assays that determine which patients might benefit from what therapy. Just as tissue biopsies are the gold standard in other cancers, performing IHC on BMBXs is a feasible method for the routine care of MM patients. The present invention provides a strong argument that determining the CC state may be a great adjunct to therapeutic strategy. Also, once CC machinery is thoroughly mapped out in MM, it promises to provide a means to develop curative drugs that can be administered with few side effects in a patient-specific manner.

The present invention provides a better understanding of the balance between positive and negative cell cycle regulators that affect the selective inactivation of Rb, and how that mechanism underlies deregulated cell cycle re-entry to promote the expansion of self-renewing MM cells and drive disease progression. In addition, the simple immunohistochemical analyses of the present invention present diagnostic and prognostic tools that are a significant improvement over the current diagnostic and therapeutic standards for cancer patients.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of determining the presence of a retinoblastoma protein (Rb)-mediated hematopoietic cancerous or pre-cancerous condition, said method comprising:

providing a patient biopsy sample as a histologic section comprising fixed hematopoietic cells;

exposing the patient sample to (i) a first antibody that recognizes phosphorylation of serine on the retinoblastoma protein (pS-Rb) and indicates that the cell bound by said first antibody has entered mid-G1 phase of cell cycle progression, and (ii) a second antibody that recognizes a cell surface or cytoplasmic marker for neoplastic hematopoietic cells; and identifying hematopoietic cells of the patient sample that are recognized by both the first and second antibodies, wherein recognition of hematopoietic cells of the patient biopsy sample by both first and second antibodies determines the presence of an Rb-mediated hematopoietic cancerous or pre-cancerous condition.

2. The method according to claim 1 further comprising:

providing a second patient biopsy sample as a histologic section comprising fixed hematopoietic cells, the second patient biopsy sample having been obtained from the same patient after a time delay;

performing said exposing and said identifying on the second patient biopsy sample; and determining whether the second patient biopsy sample, relative to the first patient biopsy sample, contains a change in the percentage of hematopoietic cells that are recognized by both the first and second antibodies, wherein an increase indicates advancement of the Rb-mediated hematopoietic cancerous or pre-cancerous condition, and a decrease indicates remission of the Rb-mediated hematopoietic cancerous or pre-cancerous condition.

3. The method according to claim 1 further comprising:

exposing the patient biopsy sample to an antibody that recognizes a nuclear cell cycling protein marker; and identifying cells in the patient biopsy sample that are recognized by the antibody that recognizes the cell cycling protein marker.

4. The method according to claim 3, wherein the nuclear cell cycling protein marker is Ki-67 or skp-2.

5. The method according to claim 1, wherein the phosphorylated serine residue of the Rb protein is selected from the group consisting of serine-608, serine-780, serine-795, and serine-807/811.

6. The method according to claim 1, wherein the patient biopsy sample is selected from the group consisting of a solid tumor containing a substantially homogenous population of cells; a heterogeneous population of non-neoplastic and neoplastic cells; and bone marrow.

7. The method according to claim 6, wherein the patient biopsy sample is from a solid tumor containing a substantially homogenous population of cells.

8. The method according to claim 6, wherein the patient biopsy sample is from a patient tissue containing a heterogeneous population of non-neoplastic and neoplastic cells.

9. The method according to claim 1, wherein the Rb-mediated hematopoietic cancerous or pre-cancerous condition is selected from the group consisting of a lymphoma/lymphoid leukemia, a B cell neoplasm, a T cell neoplasm, a plasma cell neoplasm, monoclonal gammopathy of undetermined significance (MGUS), multiple myeloma (MM), a natural killer cell (NK) neoplasm, and Hodgkin lymphoma.

10. The method according to claim 1, wherein the hematopoietic cancerous or precancerous condition is selected from the group consisting of acute myelogenous leukemia (AML), acute promyelocytic leukemia (APL); a myeloproliferative disorder (MPD); chronic myelogenous leukemia (CML); polycythemia vera; essential thrombocythemia; idiopathic myelofibrosis; myelodysplastic syndromes; myelodysplastic/myeloproliferative diseases; acute lymphoblastic leukemias (ALL); precursor B-lymphoblastic leukemia/lymphoma; precursor T lymphoblastic leukemia/lymphoma; chronic lymphocytic leukemia (CLL); histiocytic disorders and mastocytosis.

11. The method according to claim 1, wherein the cell surface marker for neoplastic hematopoietic cells is selected from the group consisting of CD20, CD3, immunoglobulinκ light chain, immunoglobulinλ light chain, CD138, CD30, CD31, CD43, CD56, CD68, CD117, and CD34.

12. The method according to claim 11, wherein the cell surface marker is CD20 and the neoplastic cell is a cancerous or pre-cancerous B-cell or popcorn cell of nodular lymphocyte predominant Hodgkin lymphoma.

13. The method according to claim 11, wherein the cell surface marker is CD3 and the neoplastic cell is a cancerous or precancerous T-cell.

14. The method according to claim 11, wherein the cell surface marker is CD138 and the neoplastic hematopoietic cell is a cancerous or precancerous plasma cell.

15. The method according to claim 11, wherein the cell surface marker is CD31 and the neoplastic cell is a cancerous or precancerous plasma cell or associated with AML or CML.

16. The method according to claim 11, wherein the cell surface marker is CD43 and the neoplastic cell is a cancerous or precancerous B-cell or a myeloid neoplasm.

17. The method according to claim 11, wherein the cell surface marker is CD56 and the neoplastic cell is associated with multiple myeloma or myeloid leukemia.

18. The method according to claim 11, wherein the cell surface marker is CD68 and the neoplastic cell is a myeloid cell.

19. The method according to claim 11, wherein the cell surface marker is CD117 and the neoplastic cell is a myeloid cell or mast cell.

20. The method according to claim 11, wherein the cell surface marker is CD34 and the neoplastic cell is a B, T, or myeloid cell.

21. The method according to claim 3 further comprising:

providing a second patient biopsy sample as a histologic section comprising fixed cells, the second patient biopsy sample having been obtained from the same patient after a time delay;

performing each said exposing and each said identifying on the second patient biopsy sample; and determining whether there exists, following the time delay, an increase in the percentage of cells in the second patient biopsy sample, relative to the first patient biopsy sample, that are identified during each said identifying, wherein an increase indicates advancement of the Rb-mediated cancerous or pre-cancerous condition, and a decrease indicates remission or a stable phase of the Rb-mediated cancerous or pre-cancerous condition.

22. A method of assessing the efficacy of cancer therapy for a retinoblastoma protein (Rb)-mediated cancer, said method comprising:

performing the method of claim 2 on the first and second patient biopsy samples, wherein the first and second biopsy samples are obtained from the patient before and after, respectively, administration of cancer therapy to the patient, and wherein a decrease in the percentage of identified cells in the second biopsy sample relative to the first biopsy sample indicates the efficacy of the cancer therapy.

23. A method of assessing the efficacy of cancer therapy for a retinoblastoma protein (Rb)-mediated cancer, said method comprising:

performing the method of claim 21 on the first and second patient biopsy samples, wherein the first and second biopsy samples are obtained from the patient before and after, respectively, administration of cancer therapy to the patient, and wherein a decrease in the percentage of identified cells in the second biopsy sample, relative to the first biopsy sample, indicates the efficacy of the cancer therapy.

24. A method of determining the presence of Rb-mediated multiple myeloma, said method comprising:

providing a patient bone marrow sample as a histologic section comprising fixed hematopoietic cells;

exposing the patient bone marrow sample to a first antibody that recognizes phosphorylation of serine on the retinoblastoma protein (pS-Rb) and a second antibody that recognizes a cell surface or cytoplasmic marker for myeloma cells; and identifying myeloma cells of the patient bone marrow sample that are recognized by both the first and second antibodies, wherein recognition of myeloma cells of the patient sample by both first and second antibodies determines the presence of an Rb-mediated multiple myeloma.

25. The method according to claim 24 further comprising:

providing a second patient bone marrow sample as a histologic section comprising fixed hematopoietic cells, the second patient sample having been obtained from the same patient after a time delay;

performing said exposing and said identifying on the second patient bone marrow sample; and determining whether the second patient bone marrow sample, relative to the first patient bone marrow sample, contains a change in the percentage of myeloma cells that are recognized by both the first and second antibodies, wherein an increase indicates the presence and advancement of the Rb-mediated multiple myeloma, and a decrease indicates a decline in the presence or remission of the Rb-mediated multiple myeloma.

26. The method according to claim 24 further comprising:

exposing the patient bone marrow sample to a third antibody that recognizes a nuclear cell cycling protein marker; and identifying cells in the patient bone marrow sample that are recognized by the third antibody.

27. The method according to claim 26, wherein the nuclear cell cycling protein marker is Ki-67 or skp-2.

28. The method according to claim 24, wherein the phosphorylated serine residue of the Rb protein is selected from the group consisting of serine-608, serine-780, serine-795, and serine-807/811.

29. The method according to claim 24, wherein the cell surface marker for myeloma cells is selected from the group consisting of CD138 and CD56.

30. The method according to claim 26 further comprising:

providing a second patient bone marrow sample as a histologic section comprising fixed hematopoietic cells, the second patient bone marrow sample having been obtained from the same patient after a time delay;

performing each said exposing and each said identifying on the second patient bone marrow sample; and determining whether there exists, following the time delay, an increase in the percentage of myeloma cells in the second patient bone marrow sample, relative to the first patient bone marrow sample, that are identified during each said identifying, wherein an increase indicates the presence and advancement of the Rb-mediated multiple myeloma, and a decrease indicates a decline in the presence or remission of the Rb-mediated multiple myeloma.

31. A method of assessing the efficacy of cancer therapy for a retinoblastoma protein (Rb)-mediated multiple myeloma, said method comprising:

performing the method of claim 25 on the first and second patient bone marrow samples, wherein the first and second bone marrow samples are obtained from the patient before and after, respectively, administration of cancer therapy to the patient, and wherein a decrease in the percentage of identified myeloma cells in the second sample relative to the first indicates a decline in the presence of myeloma cells and the efficacy of the cancer therapy.

32. A method of assessing the efficacy of cancer therapy for a retinoblastoma protein (Rb)-mediated multiple myeloma, said method comprising:

performing the method of claim 30 on the first and second patient bone marrow samples, wherein the first and second bone marrow samples are obtained from the patient before and after, respectively, administration of cancer therapy to the patient, and wherein a decrease in the percentage of identified myeloma cells in the second sample relative to the first indicates a decline in the presence of myeloma cells and the efficacy of the cancer therapy.

33. A method of determining the presence of a retinoblastoma protein (Rb)-mediated hematopoietic cancerous or precancerous condition, said method comprising:

providing a patient biopsy sample as a histologic section comprising fixed hematopoietic cells;

treating the histologic section with an agent that prevents dephosphorylation;

exposing the treated patient sample to (i) a first antibody that recognizes phosphorylation of serine on the retinoblastoma protein (pS-Rb) and indicates that the cell bound by said first antibody has entered mid-G1 phase of cell cycle progression, and (ii) a second antibody that recognizes a cell surface or cytoplasmic marker for neoplastic hematopoietic cells; and identifying hematopoietic cells of the patient sample that are recognized by both the first and second antibodies, wherein recognition of hematopoietic cells of the patient biopsy sample by both first and second antibodies determines the presence of an Rb-mediated hematopoietic cancerous or pre-cancerous condition.

34. The method according to claim 33, wherein the agent that prevents dephosphorylation is calyculin A.

*35. A method of determining the presence of a retinoblastoma protein (Rb)-mediated hematopoietic cancerous or pre-cancerous condition, said method comprising:*

*providing a patient biopsy sample as a histologic section comprising fixed hematopoietic cells;*

*exposing the patient sample to (i) a first antibody that recognizes phosphorylation of serine on the retinoblastoma protein (pS-Rb) and indicates that the cell bound by said first antibody has entered mid-G1 phase of cell cycle progression, or a first antibody that recognizes Ki-67, and (ii) a second antibody that recognizes a cell surface or cytoplasmic marker for neoplastic hematopoietic cells selected from the group consisting of CD20, CD3, CD138, CD31, CD43, CD56, CD68, CD117, and CD34; and*

*identifying hematopoietic cells of the patient sample that are recognized by both the first and second antibodies, wherein recognition of hematopoietic cells of the patient biopsy sample by both first and second antibodies determines the presence of an Rb-mediated hematopoietic cancerous or pre-cancerous condition.*

*36. The method according to claim 35 further comprising:*

*providing a second patient biopsy sample as a histologic section comprising fixed hematopoietic cells, the second patient biopsy sample having been obtained from the same patient after a time delay;*

*performing said exposing and said identifying on the second patient biopsy sample; and*

*determining whether the second patient biopsy sample, relative to the first patient biopsy sample, contains a change in the percentage of hematopoietic cells that are recognized by both the first and second antibodies,*

*wherein an increase indicates advancement of the Rb-mediated hematopoietic cancerous or pre-cancerous condition, and a decrease indicates remission of the Rb-mediated hematopoietic cancerous or pre-cancerous condition.*

*37. The method according to claim 35, wherein the patient biopsy sample is selected from the group consisting of a solid tumor containing a substantially homogenous population of cells; a heterogeneous population of non-neoplastic and neoplastic cells; and bone marrow.*

*38. The method according to claim 37, wherein the patient biopsy sample is from a solid tumor containing a substantially homogenous population of cells.*

*39. The method according to claim 37, wherein the patient biopsy sample is from a patient tissue containing a heterogeneous population of non-neoplastic and neoplastic cells.*

*40. The method according to claim 37, wherein the patient biopsy sample is from bone marrow.*

*41. The method according to claim 35, wherein the cell surface marker is CD20 and the neoplastic cell is associated with a B-cell lymphoma.*

*42. The method according to claim 35, wherein the cell surface marker is CD3 and the neoplastic cell is associated with a T-cell lymphoma.*

*43. The method according to claim 35, wherein the cell surface marker is CD138 and the neoplastic cell is associated with a plasma cell neoplasm.*

*44. The method according to claim 35, wherein the cell surface marker is CD31 and the neoplastic cell is associated with a plasma cell neoplasm in extramedullary sites.*

*45. The method according to claim 35, wherein the cell surface marker is CD43 and the neoplastic cell is associated with myeloid leukemia.*

*46. The method according to claim 35, wherein the cell surface marker is CD56 and the neoplastic cell is associated with multiple myeloma or myeloid leukemia.*

*47. The method according to claim 35, wherein the cell surface marker is CD68 and the neoplastic cell is associated with myeloid leukemia.*

*48. The method according to claim 35, wherein the cell surface marker is CD117 and the neoplastic cell is associated with acute myelogenous leukemia.*

*49. The method according to claim 35, wherein the cell surface marker is CD34 and the neoplastic cell is associated with acute lymphoblastic leukemia.*

*50. The method according to claim 35, wherein said exposing is carried out using the first antibody that recognizes Ki-67 and the second antibody that recognizes CD138.*

*51. A method of assessing the efficacy of cancer therapy for a retinoblastoma protein (Rb)-mediated multiple myeloma, said method comprising:*

*performing the method of claim 36 on the first and second patient biopsy samples, wherein the first and second biopsy samples are obtained from the patient before and after, respectively, administration of cancer therapy to the patient, and wherein a decrease in the percentage of identified myeloma cells in the second biopsy sample relative to the first biopsy sample indicates the efficacy of the cancer therapy.*

*52. A method of determining the presence of Rb-mediated multiple myeloma, said method comprising:*

*providing a patient bone marrow sample as a histologic section comprising fixed hematopoietic cells;*

*exposing the patient bone marrow sample to (i) either a first antibody that recognizes phosphorylation of serine on the retinoblastoma protein (pS-Rb) or a first antibody that recognizes Ki-67, and (ii) a second antibody that recognizes a cell surface or cytoplasmic marker for myeloma cells; and*

*identifying myeloma cells of the patient bone marrow sample that are recognized by both the first and second antibodies, wherein recognition of myeloma cells of the patient sample by both first and second antibodies determines the presence of an Rb-mediated multiple myeloma.*

*53. The method according to claim 52 further comprising:*

*providing a second patient bone marrow sample as a histologic section comprising fixed hematopoietic cells, the second patient sample having been obtained from the same patient after a time delay;*

*performing said exposing and said identifying on the second patient bone marrow sample; and*

*determining whether the second patient bone marrow sample, relative to the first patient bone marrow sample, contains a change in the percentage of myeloma cells that are recognized by both the first and second antibodies,*

*wherein an increase indicates the presence and advancement of the Rb-mediated multiple myeloma, and a decrease indicates a decline in the presence or remission of the Rb-mediated multiple myeloma.*

*54. The method according to claim 52, wherein said exposing is carried out using the first antibody that recognizes Ki-67.*

*55. The method according to claim 54, wherein the cell surface marker for myeloma cells is selected from the group consisting of CD138 and CD56.*

*56. The method according to claim 52, wherein the cell surface marker for myeloma cells is selected from the group consisting of CD138 and CD56.*

*57. A method of assessing the efficacy of cancer therapy for a retinoblastoma protein (Rb)-mediated multiple myeloma, said method comprising:*

*performing the method of claim 52 on the first and second patient bone marrow samples, wherein the first and second bone marrow samples are obtained from the patient before and after, respectively, administration of cancer therapy to the patient, and wherein a decrease in the percentage of identified myeloma cells in the second sample relative to the first indicates a decline in the presence of myeloma cells and the efficacy of the cancer therapy.*

*58. The method according to claim 33, wherein the cell surface marker for neoplastic hematopoietic cells is selected from the group consisting of CD20, CD3, CD138, CD31, CD43, CD56, CD68, CD117, and CD34.*

* * * * *